(12) United States Patent
Arnold et al.

(10) Patent No.: US 10,913,927 B2
(45) Date of Patent: Feb. 9, 2021

(54) METHOD FOR AFFECTING PHENOTYPIC ACTIVITY OF ENDOPHYTIC FUNGI

(71) Applicant: Arizona Board of Regents on Behalf of the University of Arizona, Tucson, AZ (US)

(72) Inventors: Anne Elizabeth Arnold, Tucson, AZ (US); Kayla Arendt, Tucson, AZ (US); David A. Baltrus, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/952,104

(22) Filed: Apr. 12, 2018

(65) Prior Publication Data

US 2018/0251724 A1    Sep. 6, 2018

Related U.S. Application Data

(62) Division of application No. 14/745,365, filed on Jun. 19, 2015, now Pat. No. 10,000,733.

(60) Provisional application No. 62/014,615, filed on Jun. 19, 2014.

(51) Int. Cl.
| | |
|---|---|
| *C12N 1/14* | (2006.01) |
| *C12N 1/20* | (2006.01) |
| *C12Q 1/26* | (2006.01) |
| *C12Q 1/34* | (2006.01) |
| *G01N 33/569* | (2006.01) |

(52) U.S. Cl.
CPC ............... *C12N 1/14* (2013.01); *C12N 1/20* (2013.01); *C12Q 1/26* (2013.01); *C12Q 1/34* (2013.01); *G01N 33/56961* (2013.01); *G01N 2333/37* (2013.01); *G01N 2333/942* (2013.01)

(58) Field of Classification Search
CPC .................................................... C12N 1/14
See application file for complete search history.

(56) References Cited

PUBLICATIONS

Anderson et al., Economic Botany, 1952, 6(3):294-308.*
Gilliver, Annals of Botany, 1946, vol. 10, No. 39, pp. 271-282.*
Partida-Martinez et al. Current Biology, 2007, 17:773-777.*
Lackner et al. PLoS Pathogens, 2011, 7(6):1-4.*
Sheikh, Saudi J of Biological Sciences, 2010, 17:331-339.*
Arnold, A.E., "Understanding the Diversity of Foliar Endophytic Fungi: Progress, Challenges, and Frontiers." Fungal Biology Reviews 21 (2007), pp. 51-66. Published by Elsevier Ltd. on behalf of the British Mycological Society.
Arnold, A.E, et al., "Diversity and Host Range of Foliar Fungal Endophytes: Are Tropical Leaves Biodiversity Hotspots?" Ecology. 88(3), 2007, pp. 541-549.
Bagchi, R., et al., "Pathogens and Insect Herbivores Drive Rainforest Plant Diversity and Composition." Nature. Publishers Limited, 2014, vol. 506, pp. 85-88.
Berg, G., et al., "The Plant Microbiome and its Importance for Plant and Human Health." Frontiers in Microbiology (2014), vol. 5, Article 491, pp. 5-6.
Berg, G., et al., "Unraveling the plant microbiome: looking back and future perspectives." Frontiers in Microbiology (2014), vol. 5, Article 148, pp. 1-7.
Bertaux, J., et al., "In Situ Identification of Intracellular Bacteria Related to *Paenibacillus* spp. in the Mycelium of the Ectomycorrhizal Fungus Laccaria bicolor S238N." Applied and Environmental Microbiology, Jul. 2003, vol. 69, No. 7, pp. 4243-4248.
Bianciotto, V., et al., "Vertical Transmission of Endobacteria in the Arbuscular Mycorrhizal Fungus Gigaspora margarita through Generation of Vegetative Spores." Applied and Environmental Microbiology, Jun. 2004, vol. 70, No. 6, pp. 3600-3608.
Desiro, A., et al., "Detection of a Novel Intracellular Microbiome Hosted in Arbuscular Mycorrhizal Fungi." The ISME Journal (2014) 8, pp. 257-270.
Gilbert, G.S., et al., "Phylogenetic Signal in Plant Pathogen-Host Range." Proceedings of the National Academy of Sciences of the United States of America (2007), vol. 104, No. 12, pp. 4979-4983.
Higgins, K.L., et al., "Communities of Fungal Endophytes in Tropical Forest Grasses: Highly Diverse Host- and Habitat Generalists Characterized by Strong Spatial Structure." Fungal Ecology 8 (2014), pp. 1-11.
Hoffman, M. T., et al., "Diverse Bacteria Inhabit Living Hyphae of Phylogenetically Diverse Fungal Endophytes." Applied and Environmental Microbiology, Jun. 2010, vol. 76, No. 12, pp. 4063-4075.
Hoffman, M.T., et al., "Endohyphal Bacterium Enhances Production of Indole-3-Acetic Acid by a Foliar Fungal Endophyte." PLoS One (2013), vol. 8, Issue 9, e73132, pp. 1-8.
Lewis, G.C., "Effects of Biotic and Abiotic Stress on the Growth of Three Genotypes of Lolium Perenne with and Without Infection by the Fungal Endophyte Neotyphodium lolii." Annals of Applied Biology (2004), 144:53-63.
Lindow, S.E., et al., "Microbiology of the Phyllosphere." Applied and Environmental Microbiology, Apr. 2003, vol. 69, N. 4, pp. 1875-1883.
Lumini, E., et al., "Presymbiotic Growth and Sporal Morphology are Affected in the Arbuscular Mycorrhizal Fungus Gigaspora margarita Cured of its Endobacteria." Cellular Microbiology (2007), 9(7).
Mejia, L.C., et al., "Endophytic fungi as biocontrol agents of Theobroma cacao pathogens" Biological Control 46 (2008) pp. 4-14.

(Continued)

*Primary Examiner* — Bin Shen
(74) *Attorney, Agent, or Firm* — Nguyen Tarbet LLC

(57) ABSTRACT

Described herein are methods for the alteration and/or transfer of fungal functional traits, e.g., phenotypic activity, via the controlled transfer of endohyphal symbionts, e.g., bacteria, among fungal species. Also described are methods for the identification of endohyphal bacterial symbionts as determinants of cellulase and ligninase activity in fungi, and the use of endohyphal bacterial symbionts to alter the activity, including cellulase and ligninase activities, of the fungi. In particular, the fungi described herein are endophytic fungi, that is, fungi which colonize living, and subsequently senescent, plant tissue.

12 Claims, 5 Drawing Sheets

(56) References Cited

PUBLICATIONS

Marquez, L.M., et al., "A Virus in a Fungus in a Plant: Three-Way Symbiosis Required for Thermal Tolerance." Science, Jan. 26, 2007, vol. 315, pp. 513-515 (corrected Apr. 13, 2007).

McCreadie, J.W., et al., "Context-Dependent Symbiosis Between Black Flies (*Diptera: Simuliidae*) and Trichomycete Fungi (*Harpellales: Legeriomycetaceae*)." Oikos (2005), 108:2, pp. 362-370.

Moebius, N, et al., "Active Invasion of Bacteria Into Living Fungal Cells." eLIFE (2014) 3:e03007. DOI: 10.7554/eLife.03007, pp. 1-20.

Partida-Martinez, L.P., et al., "*Burkholderia rhizoxinica* sp. nov and *Burkholderia endofungorum* sp. nov., Bacterial Endosymbionts of the Plant-Pathogenic Fungus Rhizopus microsporus." International Journal of Systematic and Evolutionary Microbiology (2007), 57:2583-2590.

Partida-Martinez, L.P., et al., "Endosymbiont-Dependent Host Reproduction Maintains Bacterial-Fungal Mutualism." Current Biology (2007), 17, pp. 773-777.

Picard, K.T., et al., "Evidence for a Facultative Mutualist Nutritional Relationship Between the Green Coccoid *Alga Bracteacoccus* sp. (*Chlorophyceae*) and the Zoosporic Fungus Rhizidium Phycophilum (*Chytridiomycota*)." Fungal Biology 117 (2013) pp. 319-328.

Sandberg, D.C., et al., "Fungal Endophytes of Aquatic Macrophytes: Diverse Host-Generalists Characterized by Tissue Preferences and Geographic Structure." Microbial Ecology (2014), 67:735-747.

Sato, Y. et al., "Detection of Betaproteobacteria inside the Mycelium of the Fungus Mortierella elongata." Microbes Environ. (2010), vol. 25, No. 4, pp. 321-324.

Singh, L.P., et al., "Unraveling the Role of Fungal Symbionts in Plant Abiotic Stress Tolerance." Plant Signaling and Behavior (2011), 6:2, pp. 175-191.

Waller, F., et al., "The Endophytic Fungus Piriformospora Indica Reprograms Barley to Salt-Stress Tolerance, Disease Resistance, and Higher Yield." Proceedings of the National Academy of Sciences of the United States of America (2005), vol. 102, No. 38, pp. 13386-13391.

Xiao, J., et al., "Secondary Metabolites from the Endophytic Botryosphaeria dothidea of Melia azedarach and Their Antifungal, Antibacterial, Antioxidant, and Cytotoxic Activities." Journal of Agricultural and Food Chemistry (2014), 62:3584-3590.

Zimmerman, N.B., et al., "Fungal Endophyte Communities Reflect Environmental Structuring Across a Hawaiian Landscape." Proceedings of the National Academy of Sciences of the United States of America (2012), vol. 109, No. 32, pp. 13022-13027.

Duponnois, et al., "The fungus-specificity of mycorrhization helper bacteria (MHBs) used as an alternative to soil Fumigation for ectomycorrhizal inoculation of bare-root Douglas-fir planting stocks with Laccaria laccata." Plant and Soil, 1993, 157:257-262.

Jaderlund, et al., "Specific interactions between arbuscular mycorrhizal fungi and plant growth-promoting bacteria: as revealed by different combinations." FEMS Microbiol Lett., 2008, 287:174-180.

Hu, et al., "Improved enzyme production by co-cultivation of Aspergillus niger and Aspergillus oryzae and with other fungi." International Biodeterioration & Biodegration, 2011, 65:248-252.

Chavez-Gomez, B., et al., "Removal of phenanthrene from soil by co-cultures of bacteria and fungi pregrown on sugarcane bagasse pith." Bioresource Technology, 2003, 89:177-183.

Frey-Klett, P., et al. "The mycorrhiza helper bacteria revisited." New Phytologist (2007) 176: 22-26.

\* cited by examiner

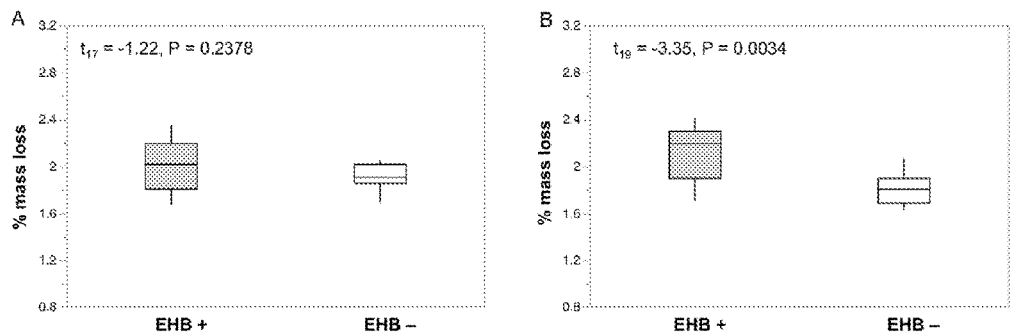
FIGURE 4
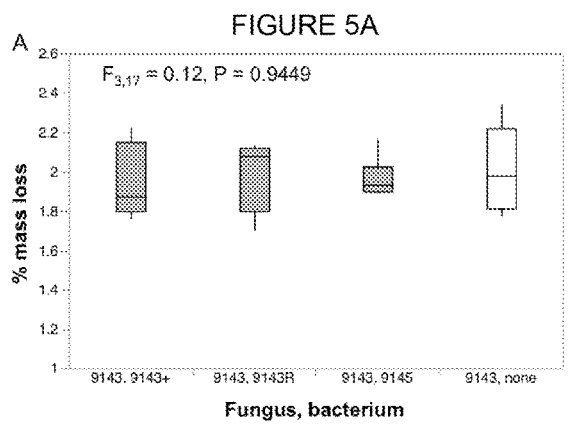
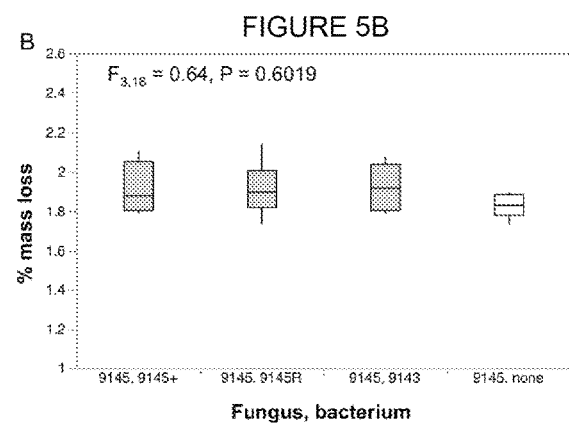
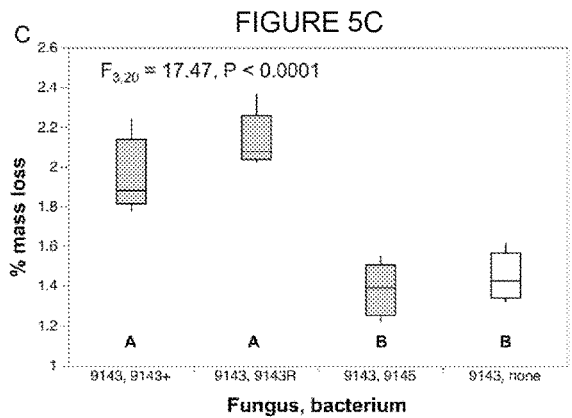
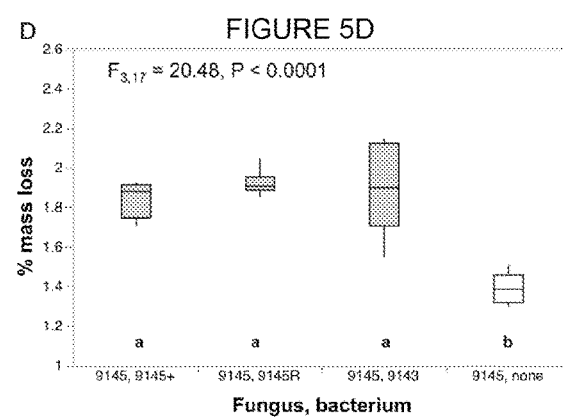

METHOD FOR AFFECTING PHENOTYPIC ACTIVITY OF ENDOPHYTIC FUNGI

CROSS-REFERENCE TO RELATED APPLICATIONS

This application is a divisional of U.S. Nonprovisional application Ser. No. 14/745,365 filed on Jun. 19, 2015, now U.S. Pat. No. 10,000,733 issued Jun. 19, 2018, and claims priority to U.S. Provisional Application No. 62/014,615 filed on Jun. 19, 2014, and the entire contents of the foregoing are incorporated herein for all legal purposes.

GOVERNMENT FUNDING

This invention was made with government support under Grant Nos. DEB1045766, DEB0702825, and IOS1354219 awarded by the National Science Foundation (NSF). The government has certain rights in the invention.

FIELD OF THE INVENTION

Plants and their associated microorganisms, for use in medical, industrial, agricultural, horticultural, forestry and other applications.

BRIEF SUMMARY OF THE INVENTION

Described herein are methods for the alteration and/or transfer of fungal functional traits, e.g., phenotypic activity, via the controlled transfer of endohyphal symbionts, e.g., bacteria, among fungal species. Also described are methods for the identification of endohyphal bacterial symbionts as determinants of cellulase and ligninase activity in fungi, and the use of endohyphal bacterial symbionts to alter the activity, including cellulase and ligninase activities, of the fungi. In particular, the fungi described herein are endophytic fungi, that is, fungi which colonize living, as well as senescent, plant tissue.

BRIEF DESCRIPTION OF THE DRAWINGS

FIG. 4 is a graph showing the results of in vitro mass-loss experimentation on *P. orientalis* foliage, including (A) fresh, green leaf material and (B) senescent leaf material treated with each of seven foliar fungi with (+) and without (−) EHB.

FIGS. 5A-5D are graphs showing in vitro mass loss from foliage of *P. orientalis* as a function of foliage state (fresh, senescent) and EHB status for each fungus.

DETAILED DESCRIPTION OF THE INVENTION

Figure 1:
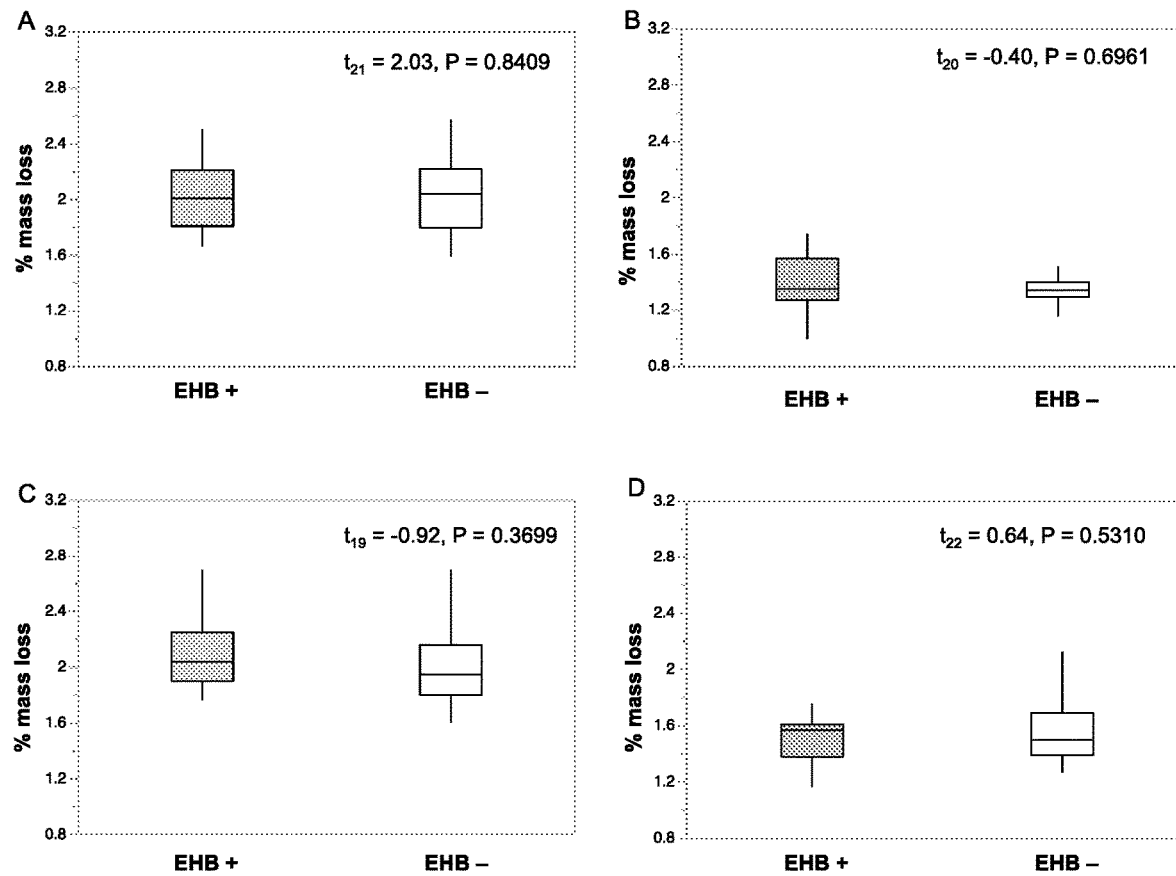
FIG. 1 is graph showing the results of in vitro mass-loss experimentation on fresh and senescent tissue of *Juniperus deppeana* and *Cupressus arizonica* as a function of treatment with seven fungi with (+) and without (−) EHB.

Plant-associated fungi provide important ecosystem functions as pathogens, mycorrhizae, endophytes and saprotrophs. Endophytic fungi colonize living plant tissues in all biomes, often providing plants with protection from pathogens, herbivores and other environmental stressors. As saprotrophs, fungi are the primary decomposers of senescent plant materials, cycling nutrients by breaking down cellulose and lignin, the major components of plant cell walls. Many fungi play more than one of these roles throughout their life cycles.

Endophytic fungi have been found to harbor (i.e., host) endohyphal bacteria (referred to herein as "EHB"). EHB live within apparently healthy, viable fungal cells. EHB of foliar fungal endophytes were first documented in endophytes of cupressaceous plants (Hoffman and Arnold 2010—Hoffman, M. and A. E. Arnold. 2010. Diverse bacteria inhabit living hyphae of phylogenetically diverse fungal endophytes. *Applied and Environmental Microbiology* 76: 4063-4075.) EHB in endophytes are distinct from bacterial endosymbionts of other plant-associated fungi, are phylogenetically diverse and can live outside their fungal hosts.

EHB can have strong effects on fungal phenotypes, influencing the interactions between fungal endophytes and the host plants of the fungal endophytes and the enzymatic and other activities of fungi in culture.

Described herein are methods for influencing plant-fungi interactions utilizing EHBs, based on the inventor's determination that the presence and identity of EHB significantly influences the success of plant infection by endophytic fungi, and that these effects display some host-specificity.

Also described herein are methods for influencing the production of cellulase and ligninase enzymes by fungi via the removal, introduction, or exchange among fungi of EHBs.

Further described herein are methods for the alteration and/or transfer of fungal functional traits, e.g. phenotypic activity, via the controlled transfer of endohyphal symbionts among foliar endophytic fungal species.

The methods described herein provide a mechanism for EHB obtained from a first fungus that is infected with that EHB, to be transferred to a second fungus of a different species than the first fungus.

Further, the methods described herein provide a mechanism to transfer EHB from a first fungus to a second fungus, wherein the second fungus is of a different class than the first fungi. For example, the first fungi could be of the class Dothideomycetes (e.g., *Microdiplodia*) and the second of the class Sordariomycetes (e.g., *Pestalotiopsis*).

The methods described herein can be applied to numerous other foliar endophytic fungi and EHB combinations. In particular, the methods described herein appear to be particularly suitable for transfer amongst species and classes within the phylum Ascomycota. The phylum Ascomycota is the most species-rich phylum of fungi. It includes diverse plant pathogens, animal pathogens, and species that produce medicinal products and pharmaceuticals, industrial products, and agents of biological control. Examples of re-synthesized or re-associated fungal-EHB "pairs" are shown in Table 1. For example, the fungus *Microdiplodia* 9145 is re-synthesized with EHB *Luteibacter* sp. 1.

Also described herein are methods for transferring endohyphal bacteria between two endophytic fungi of different species and/or different classes, comprising cross-innoculating each fungus with the bacterial inoculum of the other fungus. More specifically, a first bacterial inoculum of the EHB bacteria from a first fungus is prepared, and a second bacterial inoculum of the EHB bacteria from a second fungus is prepared, and then the first fungus is inoculated with the second EHB inoculum, and the second fungus is inoculated with the first EHB inoculum. The endophytic fungi may be of the same species, or may be of different species, or may be of different classes. The endohyphal bacteria from each fungus may be of the same species, or may be of different species, or may be of different classes or phyla/divisions.

Methods for examining phenotypic changes in endophytic fungi associated with bacterial symbiosis are described, wherein the fungi are "cured" of their endohyphal bacteria, and thereafter the activity of the fungi is examined and compared to the activity prior to "curing".

Another method involves "curing" the fungi of their endohyphal bacteria, and then inoculating the fungi with the same or different species of bacteria (to re-synthesize the symbiosis), and thereafter examining the activity of the fungi and comparing their activity from their native state, to their cured state, to their re-synthesized symbiotic state.

Also described are methods for the identification of endohyphal bacterial symbionts as determinants of cellulase and ligninase activity in fungi, and the use of endohyphal bacterial symbionts to alter the activity, including cellulase and ligninase activities, of the fungi.

Still yet another method described herein is a method for altering the phenotype(s) of endophytic fungi by "curing" and/or transferring endohyphal bacteria from a first fungus to a second fungus.

For example, the phenotype that is altered may be the enzymatic activity of the endophytic fungi. The enzymatic activity may be increased or decreased. Examples of enzymatic activity are ligninase and cellulase activity. The methods of the invention could be used in a variety of applications, such as those relevant to biofuels development from plant material, environmental remediation, etc.)

EHB presence can affect cellulase and ligninase production of fungal endophyte cultures. The effect appears to result not from enzyme production by the EHB but rather from the symbiosis of the EHB and the fungi, as illustrated by different results discussed herein when the same bacterium was present in different fungal taxa. Also, fungal cultures infected with EHB can increase degradation of plant material of native hosts.

Alternatively, the phenotype altered may be the growth rate of the endophytic fungi. Fungal growth rate can be altered by EHB presence. Growth rate of the fungi infected with EHB may be further enhanced or slowed when exposed to different nutrient and temperature conditions. EHB presence may restore fungal growth in an otherwise inviable environment.

Further, EHB can influence plant infection of fungal endophytes. Depending on the bacterium, different EHB can aid or inhibit fungal infection in closely related endophytes.

The following is an embodiment of a method according to the invention, wherein EHB is obtained from a first fungi, a second fungi is "cured" of its own naturally occurring EHB, and the EHB obtained from the first fungi is re-synthesized (i.e., re-associated) with the second fungi.

1. A fungal endophyte culture naturally infected with EHB is produced as follows: a surface-sterilized leaf tissue is cut into 2-mm² pieces and plated on nutrient media (2% Malt Extract Agar);

2. An EHB is obtained from the naturally-EHB-infected fungal endophyte culture as follows: a portion of the first fungal endophyte culture produced in Step 1 is incubated at 36° C. to induce bacterial emergence, and then the bacteria are streaked onto Luria Broth Agar (LBA); bacteria are grown in 5 mL LB at 36° C. and 200 rpm for 2 days, rinsed twice with 10 mM $MgCl_2$, resuspended in 2.4% PDB, quantified with a spectrometer and normalized to a final volume of 3 ml;

3. A fungal endophyte culture cured of EHB is produced as follows: a plug of mycelia from a second ("second" refers to the fungal-endophyte being of a different species and/or class from the first fungal endophyte used in Step 2 above) fungal endophyte culture naturally infected with EHB is transferred to fungal media amended with antibiotic [2% MEA amended with Ampicillin (100 µg/ml), Kanamycin (50 µg/ml), Tetracycline (10 µg/ml) and Ciprofloxacin (40 µg/ml)];

4. The fungal endophyte culture cured of EHB is then blended in 100 mL 2.4% Potato Dextrose Broth, and grown at 27° C. and 100 rpm for 10 days;

5. The fungal endophyte culture that has been cured of EHB (produced in Step 3) is then re-synthesized with EHB, by co-culturing it with the EHB produced in Step 2.

The following is an alternative embodiment of a method according to the invention. In this example, fungi *Pestalotiopsis* 9143 is re-associated or re-synthesized with *Luteibacter* 9143, and the step of curing the second fungi of its natural EHB infection is not described.

Culture Fungal Symbiont According to Steps 1-7, as Follows:

1. Blend a plug of mycelium (1¼ cm diameter) from inside the edge of an actively growing fungi colony (grown on 2.4% Potato Dextrose Agar) in 100 mL 2.4% Potato Dextrose Broth for 5 sec. on low 3×, transfer to sterile flask;

2. Incubate at 27° C. and 100 rpm for 10 days;

3. Collect mycelium via vacuum filtration onto a #2 Whatman filter paper;

4. Rinse mycelium with sterile water, scrape mycelia off filter paper with sterile forceps and resuspend in 2.4% PDA;

5. Blend as in step 1;

6. Quantify with a spectrophotometer (OD 600); and

7. Transfer desired amount of inoculum to sterile flasks, inoculate immediately with bacteria.

Culture Bacterial Symbiont, According to Steps 8-12, as Follows:

8. Inoculate 5 mL Luria Broth with a bacterial colony, vortex;

9. Incubate at 36° C. and 200 rpm for 3 days;

10. Centrifuge cultures at 300 rcf for 3 minutes, discard supernatant, and rinse with 4 ml of sterile 10 mM $MgCl_2$. Repeat wash;

11. Re-suspended bacteria in 4 ml 2.4% PDB; and

12. Quantify with a spectrophotometer (OD 600) and normalize to a final volume of 3 ml.

Co-Culture Symbionts According to Steps 13-17, as Follows:

13. Add 3 ml of the resuspended bacterial culture (EHB) to flasks with mycelium (fungi). The ratio of mycelium: bacteria should be 5:1 before inoculation;

14. Incubate at 27° C. and 100 rpm for 7 days;

15. Transfer 200 µL of co-culture to the center of water agar plates;

16. Incubate at 27° C. for 2 weeks; and

17. Screen the growing edge of fungal colony for EHB as described in Hoffman and Arnold, 2010 (Hoffman, M. and A. E. Arnold. 2010. Diverse bacteria inhabit living hyphae of phylogenetically diverse fungal endophytes. *Applied and Environmental Microbiology* 76: 4063-4075

Bacterial Screening to Determine Whether Fungal Isolates (i.e., Fungi "Cured of EHB") were in Fact Free of EHB.

Genomic DNA of fungal isolates were screened for bacterial infection by 16S PCR using RedTaq (Sigma) and rDNA primers 27F/1492. Positive PCR products were cleaned using ExoSAP-IT, Sanger-sequenced bidirectionally at the University of Arizona Genetics Core. Sequences were assembled automatically and basecalls made byphred and phrap with orchestration by Mesquite, followed by manual editing in Sequencher and BLAST comparisons with GenBank (U'Ren et al. 2010—U'Ren J M, Lutzoni F, Miadlikowska J, Arnold A E (2010) Community analysis reveals close affinities between endophytic and endolichenic fungi in mosses and lichens. *Microb Ecol* 60:340-353). Cultures with positive 16S products were examined for extrahyphal bacteria and viability of EHB with Invitrogen's LIVE/DEAD BacLight Bacterial Viability Kit. Negative PCR products were cloned (Agilent, StrataClone) to provide further evidence for absence of bacteria.

Ligninase and Cellulase Activity Assays.

Various cellulase and ligninase assays were conducted to show the effect on the production of cellulose and ligninase by the foliar endophytic fungi and depending upon the EHB. EHB *Luteibacter* inhibited the production of ligninase in the endophyte *Microdiplodia* 9145 and aided the production of cellulase. Endophyte *Pestalotiopsis* 9143 also harbors a bacterium from the same genus but it did not degrade cellulose regardless of infection status, and the production of ligninase was not altered with infection. Cellulase production of *Alternaria* 9055 was decreased by infection of *Sphingomonas*; however, production was enhanced for *Cladosporium* 9128 when infected with *Curtobacterium*. There was no effect of EHB on enzyme production in four of the tested endophytes.

For each fungal endophyte/EHB infection status, six petri dishes containing equal volumes of 2% Malt Extract Agar with 0.5% carboxymethylcellulose for cellulase assays (C) or water-agar with 0.05% indulin for ligninase assays (L) were each inoculated with a 6 mm plug of actively growing mycelium. Inoculated plates were incubated at 22° C. until the diameter of the colony reached 3-4 cm then flooded with 0.2% w/v Congo red (C) or with a 1.0% w/v $FeCl_3$ and $K_3[Fe(CN)]_6$ solution (L), incubated at room temperature for 40 min. and washed several times with a 1M solution of NaCl (C) or tap water (L) (Gazis et al. 2012). Fungal colony diameter and zone of clearing were then measured over two axes then averaged.

In Vitro Mass-Loss Experiment.

Dry plant material of *Platycladus orientalis* treated with EHB infected endophytes lost more mass and displayed more fungal growth than material treated with EHB-free endophytes *Platycladus orientalis* is the original host of the experimental endophytes. There was no statistically significant difference between fresh and dry material inoculated with EHB+/− fungal endophytes in that plant species, or in *J. deppeana* or *C. arizonica*.

Fresh (green) and dry (brown) leaf material was collected for three species of Cupressaceae: *Platycladus orientalis*, *Cupressus arizonica* and *Juniperus deppeana*, from branches ~1.5 m above ground at the University of Arizona Campus Arboretum. Tissue was placed in 100 mm Petri dishes (three replicate plates for each plant species/tissue type/fungal endophyte/infection status) and surface sterilized by rinsing with tap water then flooding three times with 95% EtOH (10 sec), 10% Bleach (2 min), and 70% EtOH for (2 min) (Arnold 2002). Each plate received 3 mL of sterile water and was inoculated with 75 uL of fungal inoculum prepared by grinding a 6-mm plug of actively growing mycelium (no mycelium added to the negative control) in sterile water. Plates were heavily Parafilmed, weighed immediately, then weekly for 3 weeks at which time fungal growth was scored from 0-4 ("zero" means no visible growth and "4" means 76-100% fungal growth.) Total mass loss was scaled by original weight and then by the average of the controls.

Plant Inoculations.

Three cupressaceous plants (*Platcaldus orientalis*, *Cupressus arizonica* and *Juniperus deppeana*) were inoculated with fungal suspensions prepared with one plug (6 mm in diameter) of each actively growing fungal strain grown on 2% MEA ground under sterile conditions in a 1.5 mL tube with 1.0 mL of sterile water. Suspensions without fungal material were used for controls. Healthy foliage of 4-5 branches of each of the three plant hosts were surface sterilized, allowed to air dry and immersed fully into fungal suspension (one tube per branch tip, 2 replicate tubes/strain or control/plant) and Parafilmed in place. Tubes were removed after 24 hours and branches were then bagged for 24 hours to maintain high humidity. Viability of fungal inoculums were verified from fungal suspensions directly applied to plant tissue. After two weeks, inoculated foliage was collected, cut into 10 2-$mm^2$ segments, surface sterilized then plated together on 2% MEA and incubated at room temperature. The numbers of fungal and bacterial emergences were recorded and identified based on morphology and molecular analysis.

Effect of EHB on Growth Rate Measurements.

*Luteibacter* reduces fungal growth at 25° C. for cultures grown on both water agar and malt extract agar but enhances growth for cultures grown on malt extract agar at 36° C. (EHB-*Pestalotiopsis* 9143 failed to grow at this condition). MANOVA results are reported for conditions where EHB has a significant growth effect on fungal growth rate. Error bars indicate standard error of the six replicates performed for all experiments.

Media plates (100 mm in diameter) containing 15 ml of 2% MEA or water agar were inoculated with a 6-mm pug of actively growing mycelium. Plates were incubated either at ~25° C. or 36° C. (6 replicate plates/treatment) in the dark and fungal colony diameter was measured on two axes and averaged every two days for 18 days. Plates showing bacterial emergence as well as days where the colony reached the plate edge were excluded from MANOVA analysis.

EHB Influence Plant Infection by Fungal Endophytes.

Of the isolates that maintained EHB infection during plant inoculations, endophyte *Microdiplodia* 9145/*Luteibacter* was found after introduction into *C. arizonica*. *Microdiplodia* 9140/*Rhizobium* was recovered from all three plant species. However no isolates were recovered from plant material inoculated with *Microdiplodia* 9140 (EHB−) or from the water-only control. All source inocula were confirmed to be viable.

Non-limiting examples of endophytic fungi and endohyphal bacteria that may be used to effect the production of ligninase and/or cellulase, or growth at particular temperatures or on various types of nutrient media, are as shown in Table 1 below.

TABLE 1

| Fungal endophyte (EF) | Bacterium (EB) | Water agar 25° C. | Malt agar 25° C. | Water agar 36° C. | Malt agar 36° C. | Lignin medium | Cellulose medium | Cellulase activity |
|---|---|---|---|---|---|---|---|---|
| 9140-Microdiplodia | Pantoea sp. | ns | − > + | ns | − > + | ns | ns | ns |
| 9145-Microdiplodia | Erwinia sp. | + > − | ns | ns | ns | ns | ns | ns |
| 9145-Microdiplodia | Luteibacter sp. 1 | − > + | − > + | − > + | + > − | ns | ns | + > − |
| 9055-Alternaria | Sphingomonas sp. | − > + | − > + | − > + | − > + | − > + | ns | + > − |
| 9128-Cladosporium | Burkholderia sp. | − > + | ns | − > + | ns | ns | ns | + > − |
| 9143-Pestalotiopsis | Luteibacter sp. 2 | ns | ns | + > − | ns | ns | + > − | + > − |

Table 1 shows context-dependence in the outcomes of EB-EF interactions (in the rows) and meaningful phenotypic variation among symbiotic partners (in the columns). "EB" refers to "endohyphal bacteria", and "EF" refers to "endophytic fungi". "+>−" indicates a statistically significant enhancement of growth or enzyme activity when the fungus contains the EHB (+) relative to the fungus without the EHB (−). "−>+" indicates a statistically significant enhancement of growth or enzyme activity when the fungus lacks the EHB (−) relative to the fungus that contains the EHB Not all of the combinations of fungi and bacteria shown in Table 1 result in a change cellulase activity.

Table 1 shows the significance and directionality of repeated-measures ANOVA assessing growth of clones in vitro over 14 days on water agar (low nutrient), malt extract agar (high nutrient), lignin medium (indulin as sole carbon source), and cellulose medium (carboxymethylcellulose as carbon source). Thermotolerance was assessed on two media at 36° C.

Experimental Data Regarding Ligninase Activity.

Methods.

We prepared eight fungal inocula: endophyte Pestalotiopsis 9143 harboring its native endosymbiont, Luteibacter 9143; endophyte Microdioplodia 9145 harboring its native endosymbiont, Luteibacter 9145; each endophyte growing axenically, after removal of bacterial endosymbionts via antibiotic treatments; each endophyte harboring its native endosymbiont after curing and resynthesis; and each endophyte harboring a novel endosymbiont (i.e., Pestalotiopsis 9143 with Luteibacter 9145, and Microdiplodia 9145 with Luteibacter 9143). We also prepared two bacterial inocula: Luteibacter 9143 and Luteibacter 9145 growing axenically. The axenic bacteria did not grow on the indulin medium and are excluded from analyses. For each inoculum (eight fungal, two bacterial), we inoculated six Petri dishes containing equal volumes of 2% water agar amended with 0.05% indulin. Inoculum consisted of a 6 mm plug of actively growing mycelium, or a 3-day colony of bacteria. Inoculated plates were incubated at 22° C. for 10 days (fungus) or 3 days (bacterium), then flooded with a 1.0% w/v $FeCl_3$ and $K_3[Fe(CN)]_6$ solution, incubated at room temperature for 40 min, and washed several times with sterile water (Gazis et al., 2012). Colony diameter was used as a proxy for growth rate. Clearing of the medium was noted as evidence of ligninase activity. Colony diameter and zone of clearing were quantified by averaging the diameter of the colony or clearing across two axes.

Results

1. Inoculation of Fungi by EHB can Increase Fungal Growth Rate on Indulin Medium. The Increased Growth in the Inoculated Strains May be Due to an Increased Bacterial Titer Compared to Naturally Infected Fungal Strains.

The colony diameters are close enough to normally-distributed to argue for using parametric statistics. These data appear to be grouped by trial for the associations where we had experimental replication. When analyzed together in a mixed-effects model, there was a significant effect of bacterial treatment (fixed effect) on fungal growth when accounting for variation in trial (random effect) for both Pestalotiopsis 9143 and Microdiplodia 9145.

The following results are reported for trial 2, because this trial included results from the full sampling design.

1A. Growth of Pestalotiopsis on indulin medium was influenced by bacterial treatment ($F_{3,19}$=45.2367, p<0.00013). Colony diameter when Pestalotiopsis harbored non-native Luteibacter 9145 or when reassociated native Luteibacter 9143 was significantly larger than Pestalotiopsis naturally infected with Luteibacter 9143 or the bacteria-free fungal clone (Student's t tests with Bonferroni correction, adjusted alpha=0.005).

1B. Growth of Microdiplodia on indulin medium was influenced by bacterial treatment ($F_{3,20}$=8.2273, p=0.0009). Growth of Microdiplodia on cellulose medium differed significantly as a function of bacterial status (Student's t tests and the Bonferroni adjusted alpha levels of 0.005 per test). Colony diameter when Microdiplodia harbored non-native Luteibacter 9143 or when reassociated native Luteibacter 9145 was significantly larger than Microdiplodia naturally infected with Luteibacter 9145 or the bacteria-free fungal clone (Student's t tests with Bonferroni correction, adjusted alpha=0.005).

1C. For both fungal strains, the growth rates of the strains inoculated native or non-native bacteria grew significantly better than the bacteria-free or naturally infected clones.

2. Ligninase activity (presence/absence of clearing outside or under the fungal colony) can be inhibited by presence of EHB (Microdiplodia) or EHB genotype (Pestalotiopsis).

2A. Within colony ligninase activity of both fungal strains differed qualitatively by infection status. Activity was observed in the bacteria-free clone of Microdiplodia, but not when the fungus harbored bacteria. Activity was also observed in the bacteria-free clone of Pestalotiopsis and when the fungus harbored Luteibacter 9143 but not Luteibacter 9145. Activity was consistent for all 6 replicates/trial and did not differ by trial where there was trial replication.

3. EHB Presence (Microdiplodia) or Genotype (Pestalotiopsis) can Decrease Ligninase Activity Outside the Growing Edge of the Fungal Host's Colony.

Zone of clearing scaled by colony diameter deviated significantly from a normal distribution, such that nonparametric statistics were used.

There is no trial effect of ligninase activity by bacterial treatment in either *Pestalotiopsis* or *Microdiplodia* when activity by bacterial treatment was compared with Mann-Whitney tests. Ligninase activity appears robust to fungal growth rate where we observed a difference in growth rate between the two trials.

The following results are reported for trial 2, since this trial included results from the full sampling design.

3A. Ligninase activity beyond the growing edge of *Pestalotiopsis* colonies was influenced by bacterial treatment ($\chi^2=11.8774$, df=3, p=0.0078). Activity was greater when *Pestalotiopsis* harbored native *Luteibacter* 9143 (naturally infected) than when it was free from bacteria or when it harbored *Lutiebacter* 9145 for where there was no clearing beyond the colony edge. Means were compared with Mann-Whitney tests and the Bonferroni adjusted alpha levels of 0.005 per test.

3B. Ligninase activity beyond the growing edge of *Microdiplodia* colonies was influenced by bacterial treatment ($\chi^2=22.3952$, df=3, p<0.0001). Ligninase activity outside *Microdiplodia* colonies was significantly greater and was only observed in the bacteria-free clone. Means were compared with Mann-Whitney tests and the Bonferroni adjusted alpha levels of 0.005 per test.

Experimental Data Regarding Cellulase Activity.

Methods.

We prepared eight fungal inocula: endophyte *Pestalotiopsis* 9143 harboring its native endosymbiont, *Luteibacter* 9143; endophyte *Microdioplodia* 9145 harboring its native endosymbiont, *Luteibacter* 9145; each endophyte growing axenically, after removal of bacterial endosymbionts via antibiotic treatments; each endophyte harboring its native endosymbiont after curing and resynthesis; and each endophyte harboring a novel endosymbiont (i.e., *Pestalotiopsis* 9143 with *Luteibacter* 9145, and *Microdiplodia* 9145 with *Luteibacter* 9143). We also prepared two bacterial inocula: *Luteibacter* 9143 and *Luteibacter* 9145 growing axenically. For each inoculum (eight fungal, two bacterial), we inoculated six Petri dishes containing equal volumes of 2% malt extract agar amended with 0.5% carboxymethylcellulose. Inoculum consisted of a 6 mm plug of actively growing mycelium, or a 3-day colony of bacteria. Inoculated plates were incubated at 22° C. for 10 days (fungus) or 3 days (bacterium), then flooded with 0.2% w/v Congo red solution, incubated at room temperature for 40 min, and washed several times with 1 M NaCl (Gazis et al., 2012). Colony diameter was used as a proxy for growth rate. Clearing of the medium was noted as evidence of cellulase activity. Colony diameter and zone of clearing were quantified by averaging the diameter of the colony or clearing across two axes.

Results

1. EHB Genotype can Influence Fungal Growth Rate on Cellulose Medium (Proxy=Colony Diameter).

The colony diameters are close enough to normally-distributed to argue for using parametric stats. These data appear to be grouped by trial for the associations where we had experimental replication. When analyzed together in a mixed-effects model, there was a significant effect of bacterial treatment (fixed effect) on fungal growth when accounting for variation in trial (random effect) for both *Pestalotiopsis* 9143 and *Microdiplodia* 9145.

The following results are reported for trial 2, because this trial included results from the full sampling design.

1A. Growth of *Pestalotiopsis* on cellulose medium was influenced by bacterial treatment ($F_{3,20}=6.0135$, p=0.0043). Colony diameter when *Pestalotiopsis* harbored the non-native *Luteibacter* 9145 was significantly smaller than when *Pestalotiopsis* harbored *Luteibacter* 9143 or had no bacterium (Student's t tests with Bonferroni correction, adjusted alpha=0.005). Colony diameter was similar when *Pestalotopsis* harbored *Luteibacter* 9143 or no bacterium. Colony diameter was significantly reduced when *Pestalotiopsis* harbored the non-native *Luteibacter* 9145.

1B. Growth of *Microdiplodia* on cellulose medium was influenced by bacterial treatment ($F_{3,20}=49.7930$, p<0.0001). Growth of *Microdiplodia* on cellulose medium differed significantly as a function of bacterial status (Student's t tests and the Bonferroni adjusted alpha levels of 0.005 per test). Colony diameter when *Microdiplodia* harbored the non-native *Luteibacter* 9143 was significantly greater than when *Microdiplodia* harbored *Luteibacter* 9145 or had no bacterium.

1C. For both fungal strains, only the growth rate of the strain inoculated with the non-native bacterium significantly differed from the bacterium-free clone. In each case growth rate did not differ for fungi in the presence of their native bacterium vs. when growing axenically (i.e., with no bacterium). Growth of *Pestalotiopsis* 9143 was significantly reduced relative to axenic strains by the presence of the non-native bacterium 9145. Growth of *Microdiplodia* with 9143 was significantly slower than that of *Pestalotiopsis* 9143 when the same bacterial strain was present in each. Growth of *Microdiplodia* 9145 with bacterium 9143 was significantly faster than growth of *Microdiplodia* alone. In both cases, strains that harbored *Luteibacter* 9143 tended to grow more than strains that harbored *Luteibacter* 9145.

2. Cellulase Activity (Presence/Absence of Clearing Outside or Under the Colony) is Only Observed in the Presence of EHB.

2A. Within colony cellulase activity of both fungal strains differed qualitatively by infection status. Activity was observed when *Microdiplodia* and *Pestalotiopsis* harbored *Luteibacter* 9143 or *Luteibacter* 9145. No activity was observed in the bacteria-free clones. Activity was consistent for all 6 replicates/trial and did not differ by trial where there was trial replication.

3. EHB Genotype can Increase Cellulase Activity Outside the Growing Edge of the Fungal Host's Colony. Without Bacteria, No Activity Outside the Colony was Present in Either Fungal Strain.

Zone of clearing scaled by colony diameter deviated significantly from a normal distribution, such that nonparametric statistics were used. There is no trial effect of cellulase activity by bacterial treatment in either *Pestalotiopsis* or *Microdiplodia* when activity by bacterial treatment was compared with Mann-Whitney tests. Cellulase activity appears robust to fungal growth rate where we observed a difference in growth rate between the two trials. As shown in, zone of cellulose clearing scaled by fungal colony diameter of both trials grouped by fungal strain (*Pestalotiopsis* 9143 or *Microdiplodia* 9145, bacterial strain (*Luteibacter* 9143 or 9145) and type of association (+=naturally infected, R=re-associated). Data points from trial 2 are gray and data from trial 1 are black.

The following results are reported for trial 2, since this trial included results from the full sampling design.

3A. Cellulase activity beyond the growing edge of *Pestalotiopsis* colonies was influenced by bacterial treatment ($\chi^2=9.774$, df=3, p=0.0206). Activity was greater when *Pestalotiopsis* harbored native *Luteibacter* 9143 than when it was free from bacteria or when it harbored *Luteibacter* 9145 for where there was no clearing beyond the colony edge when compared with Mann-Whitney tests and the Bonferroni adjusted alpha levels of 0.005 per test.

3B. Cellulase activity beyond the growing edge of *Microdiplodia* colonies was influenced by bacterial treatment ($\chi^2$=13.3295, df=3, p=0.004). Cellulase activity outside *Microdiplodia* colonies differed significantly as a function of infection status when compared with Mann-Whitney tests and the Bonferroni adjusted alpha levels of 0.005 per test. Activity was significantly greater when *Microdiplodia* harbored *Luteibacter* 9143 or *Luteibacter* 9145 compared to the bacteria-free clone for which there was no activity outside the colony.

Conclusions.

Cellulase production is robust to variation in fungal growth rates. Infection by a non-native bacterium has the greatest influence on fungal growth rate, and the direction of change is dependent on the type of association. Cellulase activity was only observed in fungal strains that harbored bacteria and the axenic bacteria. The degree of activity may be influenced by the bacterial genotype in *Pestalotiopsis*. In all responses examined for native associations, naturally infected fungal phenotypes were recovered in the re-associated strains suggesting bacterial presence is responsible for altering fungal phenotypes in natural associations.

Experimental Data Illustrating Transfer of EHB Between Fungi from Different Classes of Ascomycota.

The following describes methods for successfully reintroducing (re-synthesizing or re-associating) EHB into axenic fungal mycelia, and illustrates that the identity of the fungal host and culture conditions can define the establishment of these widespread and important symbioses. We first establish in vitro conditions favoring reintroduction of two strains of EHB (*Luteibacter* spp.) into axenic strains of their original fungal hosts, focusing on two fungi originally isolated from healthy plant tissue as endophytes: *Microdiplodia* sp. (Dothideomycetes) and *Pestalotiopsis* sp. (Sordariomycetes). We show that reintroduction was successful for *Microdiplodia/Luteibacter* on potato dextrose agar and water agar, but was only successful for *Pestalotiopsis/Luteibacter* on water agar. We demonstrate that these EHB can be introduced to a novel fungal host under the same conditions, successfully transferring EHB between fungi representing different classes of Ascomycota. Finally, we manipulate conditions to optimize reintroduction in a focal EHB/fungal association, altering the nutrient content for the co-culture medium, the mycelium:bacteria ratio in co-culture, the age of the bacterial culture at the time of co-culturing, treatment of the axenic cultures prior to co-culturing, and the nutrient content of the solid medium onto which the co-culture was plated. We show that EHB infections were initiated and maintained more often under low-nutrient culture conditions and when EHB and fungal hyphae were washed with $MgCl_2$ prior to re-association.

Here we examine methods for successfully reintroducing EHB into axenic fungal mycelia, with a focus on two species representing distantly related clades of Ascomycota that were originally isolated as foliar endophytes from a woody plant. We first establish in vitro conditions favoring reintroduction of two different strains of axenic EHB (*Luteibacter* sp., Gammaproteobacteria) into axenic strains of their original fungal hosts. We then demonstrate that these EHB can be introduced to novel fungal hosts under the same conditions, successfully transferring EHB between members of the Dothideomycetes and Sordariomycetes. Finally, we manipulate conditions to optimize reintroduction in a focal EHB/fungal association, examining the importance of the nutrient content for the co-culture medium, the mycelium:bacteria ratio in co-culture, the age of the bacterial culture at the time of co-culturing, treatment of the axenic cultures prior to co-culturing, and the nutrient content of the solid medium onto which the co-culture was plated.

Our study provides a new suite of methods for experimental assessment of the effects of EHB on fungal phenotypes, and suggests that both the fungal host and culture conditions can influence the establishment of these widespread and important symbioses. By understanding how these symbioses are initiated and maintained, we can gain new insights into the cryptic ecological interactions that shape ubiquitous plant-fungal associations. In turn, by manipulating EHB/fungal interactions in new ways, we can potentially influence fungal phenotypes for diverse human applications.

Materials and Methods

As part of a previous study, endophytes were isolated from healthy, surface-sterilized foliage of *Platycladus orientalis* (Cupressaceae) in Durham, N.C. (Hoffman and Arnold 2010). This collection included *Pestalotiopsis* sp. 9143 (Amphisphaeriaceae, Xylariales, Sordariomycetes) with its naturally occurring bacterial symbiont, *Luteibacter* sp. 9143; and *Microdiplodia* sp. 9145 (Botryosphaeriaceae, Botryosphaeriales, Dothideomycetes) with its naturally occurring symbiont, *Luteibacter* sp. 9145. Although the fungi represent distinct classes of Ascomycota, the bacteria are closely related: their 16 S rRNA sequences are 100% identical, and whole genome sequences are nearly invariant (Baltrus et al. in prep). Both associations are accessioned as living cultures at the Robert L. Gilbertson Mycological Herbarium at the University of Arizona (accessions MYCO-ARIZ 9143 and 9145).

Preparation of Axenic Cultures

Each fungal strain was cured of EHB by cultivation on 2% malt extract agar (MEA) amended with four antibiotics: ampicillin (100 µg/ml), kanamycin (50 µg/ml), tetracycline (10 µg/ml), and ciprofloxacin (40 µg/ml) (see Fisher et al. 1996, Rodrigues 1994, Lodge et al. 1996, Gamboa and Bayman 2001, Hoffman and Arnold 2010). We confirmed that fungal cultures were free of EHB using the methods described below.

EHB were isolated from naturally infected fungal cultures on 2% MEA (see Hoffman and Arnold 2010) that were incubated for 72 h at 36° C. At this temperature, bacteria emerged from hyphae and were isolated by streaking onto Luria broth (LB) agar (Bertani 1952). Unless otherwise stated, axenic fungal strains were maintained on 2% MEA at 25° C. and axenic bacterial strains were maintained in LB at 25° C.

Reintroduction of EHB into Axenic Host Fungi

We first reintroduced EHB into axenic strains of their native host fungus (i.e., *Luteibacter* sp. 9143 in *Pestalotiopsis* sp. 9143, and *Luteibacter* sp. 9145 in *Microdiplodia* sp. 9145). Prior to reassociation, the fungal and bacterial strains were prepared as follows.

For each axenic fungus, a plug of mycelium (1.25 cm diameter) was collected under sterile conditions from inside the edge of an actively growing colony on 1×potato dextrose agar (PDA, 2.4%). Each plug was separately blended in three 5 sec, high-speed pulses in a sterile blender (Waring 51BL31) in 100 mL 1× potato dextrose broth (PDB), and then transferred to a sterile flask and incubated on a rotary shaker at 27° C. and 100 rpm for 7 d. Mycelium was collected via vacuum filtration onto 8 µm Whatman filter papers, washed twice with sterile 10 mM $MgCl_2$, removed from the filter papers with forceps under sterile conditions, resuspended in 100 mL of 1×PDB, and blended as before. Removing or diluting the supernatant from liquid axenic cultures in a neutral buffer prior to co-culturing is common in microbial competition studies (Lenski et al. 1991, Jankowska et al. 2008) to maintain an osmotic balance between the internal and external environment of the cells.

Bacterial cultures were first grown on LB agar and then inoculated into 5 mL of LB and incubated on a rotary shaker at 36° C. and 200 rpm for 3 d. Cultures then were centrifuged at 300 rcf for 3 min and the supernatant was discarded. The pelleted cells were washed twice with 4 mL of sterile 10 mM $MgCl_2$ and resuspended in 4 mL of 1×PDB.

Before reassociation, fungal and bacterial suspensions were evaluated with a spectrophotometer (OD 600), normalized with respect to axenic bacterial inocula (5:1 mycelium:bacteria), and added to 50 mL of 1×PDB. Because we observed no selectable phenotype for the reassociated strains when grown on standard fungal media, we chose this ratio because at higher concentrations of bacteria, we often observed bacteria growing epihyphally on fungal cultures. The resulting mixture was cultured for 7 d at 27° C. in full darkness, with agitation on a rotary shaker at 100 rpm.

Each co-culture was prepared twice. After incubation, 20 μl of each co-culture was transferred to six Petri dishes containing nutrient media: three plates contained 1×PDA and three contained water agar. Plates were incubated at 27° C. for 14 d. Bacterial infection status was verified as described below. The success of establishing symbioses was consistent across all replicates on each medium for each EHB/fungal association. After successful infection, fungi were subcultured three times on 2% MEA to confirm the stability of the association.

We also attempted to reassociate two additional EHB/foliar fungal associations described in Hoffman and Arnold (2010): *Phyllosticta* sp. 9135 (Dothideomycetes) with its *Luteibacter* sp., and *Botryosphaeria* sp. 9133 (Dothideomycetes) with its *Luteibacter* sp. Neither of these associations was reassociated successfully under the conditions above, and thus these trials are excluded from the results.

Cross-Inoculation

Next, EHB were introduced into axenic strains of the alternate fungal hosts (i.e., *Luteibacter* sp. 9145 in *Pestalotiopsis* sp. 9143, and *Luteibacter* sp. 9143 in *Microdiplodia* sp. 9145). All methods followed those described above.

Manipulation of Resynthesis Conditions

We focused on the association of *Pestalotiopsis* sp. 9143 with *Luteibacter* sp. 9143 to further examine culture conditions under which EHB could be introduced. Using conditions that permitted successful reassocation as a baseline protocol (above), we altered the nutrient content for the co-culture medium (1×, 0.1×, 0.01×, 0.001×, and 0.0001× PDB) and the mycelium:bacteria ratio in the co-culture (10:1, 7:1, and 5:1). We also examined the role of the age of the bacterial culture at the time of co-culturing (1 day old vs. 3 days old), whether axenic cultures were washed with $MgCl_2$ before co-culturing, and the nutrient content of the solid medium onto which the co-culture was plated (water agar vs. 1×PDA). For this experiment, we adjusted the co-culture volume to 5 mL to include more replicates. Co-cultures were then incubated for 3 d in culture tubes. Each treatment was replicated twice and one fungal colony from each replicate was screened for EHB. The role of resynthesis conditions was quantified using nominal logistic analysis, with success of association as the response variable (yes, no) and the above treatments as explanatory variables.

Successful association (i.e., 'yes') was defined by detection of the bacterium using molecular analysis and confirmation that the bacteria were viable, endohyphal, and occurring within viable fungal hyphae based on visualization, as described below.

Molecular Analysis and Identification of EHB

Genomic DNA was extracted directly from fresh fungal mycelium collected from inside the growing edge of a fungal colony using a modified protocol from the Extract-N-Amp tissue PCR kit (Sigma-Aldrich). Genomic DNA was screened for the presence of bacteria by 16 S rRNA PCR using RedTaq (Sigma) with primers 27 F/1492 (Lane 1991). PCR conditions followed Hoffman and Arnold (2010) with the following amendments: 50° C. annealing temperature and 40 cycles.

Positive 16 S rRNA PCR products were cleaned using ExoSAP-IT (Affymetrix) and Sanger-sequenced bidirectionally at the University of Arizona Genetics Core. Sequences were assembled automatically, bases called, and quality scores assigned by phred (Ewing and Green 1998) and phrap (Ewing et al. 1998) with orchestration by Mesquite v. 1.06 (Maddison and Maddison 2011). Consensus sequences were edited manually in Sequencher 5.1 (Gene Codes Corporation) and compared against sequences obtained from the same specimens by Hoffman and Arnold (2010).

In all cases, sequences of bacteria obtained here were 100% identical to those reported previously from these cultures (Hoffman and Arnold 2010). Sequences also were BLASTed against GenBank (BLASTn, highly similar sequences; Altschul et al. 1990, Benson et al. 2014). Taxonomic placement within *Luteibacter*, validated previously by phylogenetic analysis (Hoffman et al. 2013), was confirmed using a ≥99% match over the full sequence length. As needed, the same methods were used to confirm the identity of EHB growing axenically.

We did not identify any additional EHB or free-living bacteria in the fungal cultures used in this study. Negative PCR products (i.e., those for which no bands were evident after 16 S rRNA PCR) were cloned (Agilent, StrataClone) following the manufacturer's instructions for reactions using half volumes. No positive clones were recovered from fungi after antibiotic treatment or from negative controls.

Visualization Methods

Molecular analyses were coupled with visual assessments to confirm that EHB were viable and were present within living fungal hyphae. Visual assessments consisted of microscopy and staining using the LIVE/DEAD BacLight Bacterial Viability Kit (Invitrogen) following Hoffman and Arnold (2010).

To prepare fungal samples for visualization, fresh hyphae were scraped from the surface of the growing edge of each fungal colony on 2% MEA. Axenic bacteria were prepared by scraping a single colony from LB agar. Hyphae or bacterial cells were placed on a glass slide with 15 μl of 1:1:18 LIVE/DEAD stain (component A: component B: $diH_2O$), covered with a coverslip, and incubated in darkness for 20 min. Sterile distilled water then was pulled through the slide mount with blotting paper. Slides were sealed with clear acrylic nail polish, which was allowed to dry before viewing. A Leica 4000 MB compound microscope with a 100-W mercury arc lamp was used for fluorescent imaging at room temperature with a Chroma Technology 35002 filter set (480-nm excitation/520-nm emission) and 100×APO oil objective. Three replicate slides were prepared per fungal culture, and in all cases, replicates from the same material were consistent.

Results

Both *Pestalotiopsis* sp. 9143 and *Microdiplodia* sp. 9145 were viable on 1×PDA and water agar in the presence and absence of EHB. Each strain of *Luteibacter* was viable on LB agar and in LB under the conditions described above, and could be isolated reliably following heat treatment of infected mycelia. EHB could be detected reliably from the original cultures using the above molecular and visualization methods, and were confirmed to be absent following antibiotic treatment.

Reintroduction of EHB

EHB were successfully reintroduced to their original host strains after those fungi were treated with antibiotics. In each case the bacteria were confirmed to be endohyphal and viable. Reinfected strains resembled the naturally infected strains with regard to hyphal morphology.

Reintroduction of *Luteibacter* sp. 9145 into *Microdiplodia* sp. 9145 was successful when the co-culture was plated on PDA or water agar. However, reintroduction of *Luteibacter* sp. 9143 into *Pestalotiopsis* sp. 9143 was only successful on water agar. In each case, reinfected fungal strains maintained these associations through at least three subculturing events on 2% MEA. Reisolation and confirmation of bacterial identity following reintroduction is now being completed.

Cross-Inoculation of EHB

*Luteibacter* sp. 9143 was successfully introduced into *Microdiplodia* sp. 9145 when the co-culture was plated on either PDA or water agar. *Luteibacter* sp. 9145 was successfully introduced into *Pestalotiopsis* sp. 9143 when the co-culture was plated on water agar. In each case, bacteria were confirmed to be endohyphal and viable and were maintained in their novel fungal hosts through at least three subculturing events on 2% MEA. Reinfected strains resembled the naturally infected strains with regard to hyphal morphology and the density of bacterial cells. Reisolation and confirmation of bacterial identity following reintroduction is now being completed.

Manipulation of Resynthesis Conditions

We examined the effects of particular culture conditions on reintroduction of EHB by focusing on the association between *Pestalotiopsis* sp. 9143 and *Luteibacter* sp. 9143. A total of 120 trials was conducted, each representing a bacterial culture of a given age (1 day old or 3 day old); washing of axenic cultures with $MgCl_2$ or not; various concentrations of the medium in which the co-culture was grown (1×, 0.1×, 0.01×, 0.001×, and 0.0001×PDB); various mycelium:bacteria ratios in the co-culture (10:1, 7:1, and 5:1); and cultivation of the co-culture on 1×PDA or water agar. All treatment combinations and their outcomes are shown in Table 2.

Nominal logistic analysis revealed that when all culture conditions were considered, those most relevant for successful resynthesis were (1) whether the axenic cultures were washed in $MgCl_2$, (2) the concentration of PDB in which the co-culture was grown, and (3) the solid medium on which the co-culture was plated. Culture age and the ratio of mycelium:bacteria were less important in the overall analysis.

In vitro reassociation of *Pestalotiopsis* sp. 9143 and *Luteibacter* sp. 9143 always failed when axenic cultures were not washed with $MgCl_2$ and when co-cultures were cultivated in 0.0001×PDB, and failed in 29 of 30 trials when the co-cultures were plated on 1×PDA. This table shows qualitative outcomes of resynthesis attempts when cultures were washed with $MgCl_2$, PDB concentrations were >0.0001×, and co-cultures were plated on water agar for resynthesis attempts started with 1- and 3-day old bacterial cultures. Nominal regression of this reduced data set did not reveal significant differences among the suites of treatments listed here; however, we note that resynthesis was always successful when 0.01×PDB was used as the co-culture medium, whereas success was more variable on other concentrations of PDB.

Examination of the data revealed that resynthesis failed in all 60 trials in which axenic cultures were not washed with $MgCl_2$. We thus excluded those 60 trials from further analysis. Among the remaining 60 trials, resynthesis was more often successful when the co-culture was plated on water agar rather than on 1×PDA: only one of 30 resynthesis attempts using PDA was successful (3 d old bacterial culture, 0.01×PDB, 7:1 mycelium:bacteria ratio, whereas 18 of 30 resynthesis attempts were successful using water agar. We thus excluded the 30 trials on PDA from further analysis. These findings are consistent with the results with our initial assessment of the influence of the culture medium on the success of reintroducing *Luteibacter* 9143 into *Pestalotiopsis* 9143.

Among the remaining 30 trials, all resynthesis attempts were unsuccessful when the co-culture was grown in 0.0001×PDB, but some resynthesis attempts were successful on each of the remaining concentrations of PDB. We thus excluded the trials on 0.0001×PDB from further analysis.

We then analyzed the remaining data set to more precisely evaluate the importance of the age of the bacterial culture, the concentration of PDB (1×, 0.1×, 0.01×, 0.001×), and the ratio of the mycelium:bacteria in co-culture establishment. Nominal regression of this reduced data set did not reveal significant differences among the suites of treatments listed here (simplified whole model, $\chi^2$=8.57, df=6, P-0.1993; no significant effects of any factor: P-0.2659, P=0.1009, and P=0.04009, respectively). However, resynthesis was always successful when 0.01×PDB was used as the co-culture medium, whereas success was more variable on other concentrations of PDB.

The present aforementioned study demonstrates resynthesis in an association with foliar fungal endophytes in the species-rich Ascomycota, which includes the vast majority of endophytic and plant-pathogenic fungi of relevance to agriculture and natural systems. This also demonstrates resynthesis involving Gammaproteobacteria, which are common in foliar endophytes studied to date, and can have profound effects on fungal. We demonstrate resynthesis for two strains of EHB and two distantly related fungi, and demonstrate that EHB can be moved between fungal strains.

The present study focused on two closely related bacteria. We believe that EHB of foliar fungi that are horizontally acquired are not host specific, although an important caveat is that all work to date has relied only on 16S rRNA sequences to differentiate bacterial strains. Such an approach alone would indicate that *Luteibacter* sp. 9143 and 9145 are of the same species; their 16 S rRNA sequences are 100% identical, and whole genome sequences are nearly invariant.

Facultative Symbioses

We found that the EHB association was facultative in these foliar fungi. Both fungi and bacteria could be grown axenically on standard media.

Nutrient Conditions

Reassociation was successful for both *Pestalotiopsis* sp. 9143/*Luteibacter* sp. 9143 and *Microdiplodia* sp. 9145/*Luteibacter* sp. 9145 on low-nutrient media (water agar). When grown on water agar, hyphae of both fungal species were sparse, transparent, and thin; in contrast, both strains had robust, dense, and pigmented or opaque hyphae on PDA. Resynthesis of *Microdiplodia* sp. 9145 with *Luteibacter* 9145 also was successful on high-nutrient media. Cross-infection of both fungal hosts with novel EHB displayed the same patterns as those observed with their native EHB.

We found that available nutrients in the culture medium strongly influenced the success of establishing EHB symbioses. Additionally, resynthesis was only successful when both axenic cultures were washed with $MgCl_2$, implying the presence of biological inhibitors that were removed upon washing. This is not surprising as many microbes will exude antimicrobial compounds that can interfere with the functions of closely related species or organisms in different kingdoms (Brian and Hemming 1947, Be'er et al. 2008). This competition is especially common between microbial endophytes (Strobel et al. 2004).

Manipulation of Culture Conditions

Our results suggest that when cultures are washed with $MgCl_2$, PDB concentrations are ca. 0.001× or greater, and co-cultures are plated on water agar, resynthesis of *Pestalotiopsis* sp. 9143/*Luteibacter* sp. 9143 can be achieved at various ratios of mycelium:bacteria (5:1, 7:1, 10:1), various concentrations of PDB (1×, 0.1×0.01×, 0.001×), and with 1 or 3 d old bacterial cultures. Qualitative examination of the results indicates that the most consistent success was obtained using 0.01×PDB, but these different suites of conditions did not differ statistically.

When comparing resynthesis success with 1 vs. 3 day old bacterial cultures, we observed the trend that trials started with the 3 day old bacterial culture reestablished symbiosis when the mycelium:bacteria ratio was lower and when the nutrient content of the co-culturing medium was higher than trials started with the 1 dayold culture. This could be due to a difference in the growth stage of the bacterium at the time of co-culturing. We also noted that when co-cultures started with the 1 day old bacterial culture were plated on 1×PDA after cultivation in 1×PDB, viable bacteria often were observed living outside of fungal cells. As such, resynthesis per se could not be verified. We therefore were conservative in our analyses and treated these as unsuccessful reintroductions.

Experimental Data Illustrating the Effects of Two Closely Related EHBs of the Genus *Luteibacter* on Substrate Use, Cellulase Activity, Ligninase Activity and Plant Tissue Degradation.

FIGS. 1-6 illustrate the results of various tests described below.

FIG. 1 shows results of in vitro mass-loss experiment on fresh and senescent tissue of *Juniperus deppeana* and *Cupressus arizonica* as a function of treatment with seven fungi with (+) and without (−) EHB. (A) fresh material of *J. deppeana*, (B) senescent material of *J. deppeana*, (C) fresh material of *C. arizonica*, and (D) senescent material of *C. arizonica*. Error bars represent standard error about the mean. Different letters indicate significantly different means from post hoc tests.

Figure 2:
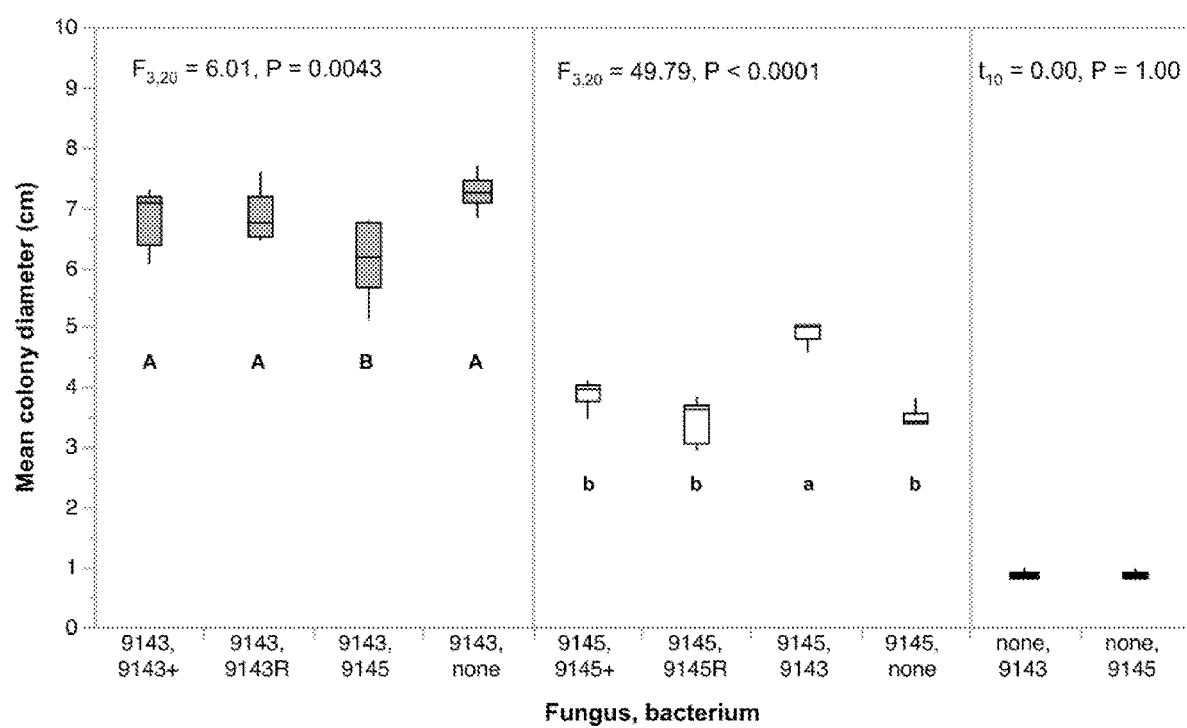
FIG. 2 is a graph showing the mean colony diameter of *Pestalotiopsis* sp. 9143, *Microdiplodia* sp. 9145, and axenic bacteria during cellulase assays as a function of EHB (*Luteibacter* sp. 9143 or *Luteibacter* sp. 9145) and type of association.

FIG. 2 shows mean colony diameter of *Pestalotiopsis* sp. 9143, *Microdiplodia* sp. 9145, and axenic bacteria during cellulase assays as a function of EHB (*Luteibacter* sp. 9143 or *Luteibacter* sp. 9145) and type of association (+=naturally infected, R=re-associated, none=no bacterium/axenic). Error bars represent one standard error. Different letters indicate significantly different means from post hoc tests.

Figure 3:
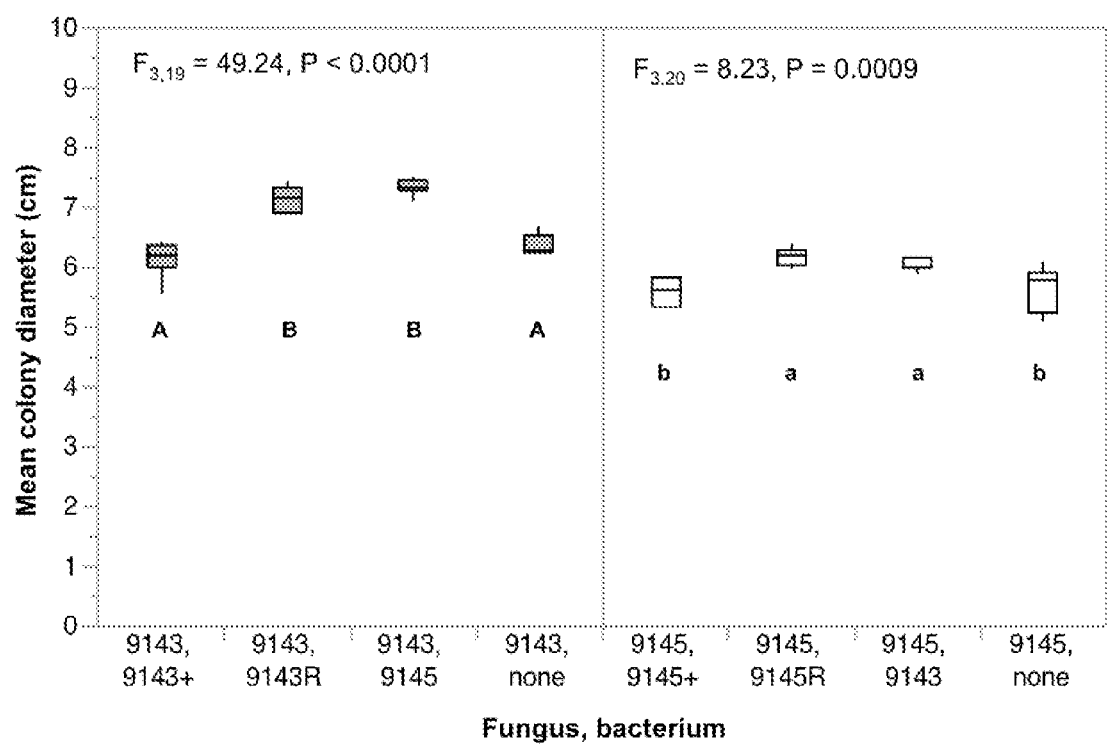
FIG. 3 is a graph showing the average colony diameter of *Pestalotiopsis* sp. 9143 or *Microdiplodia* sp. 9145 on indulin medium as a function of bacterial strain (*Luteibacter* sp. 9143 or *Luteibacter* sp. 9145) and type of association.

FIG. 3 shows average colony diameter of *Pestalotiopsis* sp. 9143 or *Microdiplodia* sp. 9145 on indulin medium as a function of bacterial strain (*Luteibacter* sp. 9143 or *Luteibacter* sp. 9145) and type of association (+=naturally infected, R=re-associated, none=no bacterium/axenic). Error bars represent one standard error. Different letters indicate significantly different means from post hoc tests.

FIG. 4 shows results of in vitro mass-loss experiment for *P. orientalis* foliage, including (A) fresh, green leaf material and (B) senescent leaf material treated with each of seven foliar fungi with (+) and without (−) EHB. Error bars represent standard error about the mean. Different letters indicate significantly different means from post hoc tests.

FIG. 5 shows in vitro mass loss from foliage of *P. orientalis* as a function of foliage state (fresh, senescent) and EHB status for each fungus. (A) *Pestalotiopsis* sp. 9143, fresh material; (B) *Microdiplodia* sp. 9145, fresh material; (C) *Pestalotiopsis* sp. 9143, senescent material; (D) *Microdiplodia* sp. 9145, senescent material. Type of association: +=naturally infected, R=re-associated, none=no bacterium. Error bars represent standard error about the mean. Different letters indicate significantly different means from post hoc tests.

Figure 6:
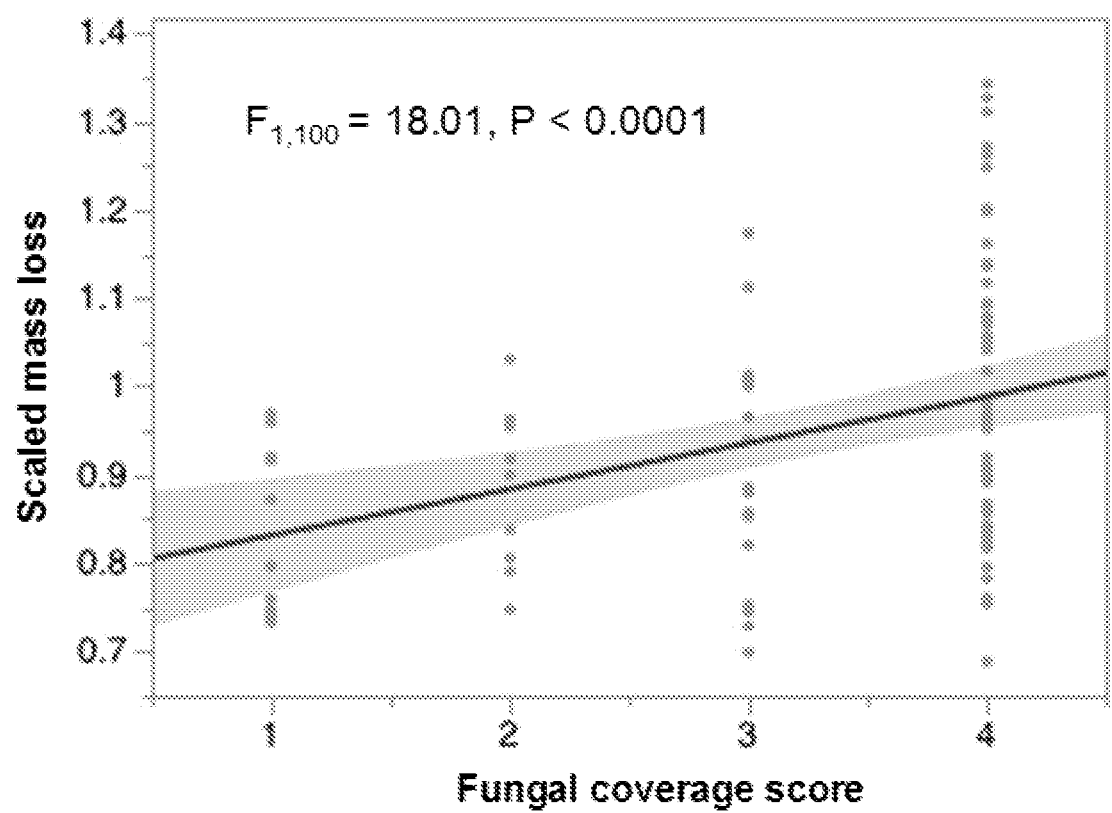
FIG. 6 is a graph showing the relationship of mass loss vs. the visual score of fungal growth, with the 95% confidence interval for the linear fit shaded along the best-fit line.

FIG. 6 shows the relationship of mass loss vs. the visual score of fungal growth, with the 95% confidence interval for the linear fit shaded along the best-fit line.

We manipulated two endophyte/EHB associations to examine enzyme activity and measure the resulting effects on plant tissue degradation. We found that the presence and identity of EHB significantly influenced fungal growth and cellulase and ligninase activity in a partnership-specific manner. Relative to axenic controls, fungal cultures infected with EHB grew significantly more rapidly on, and led to greater mass loss from, senescent tissue of their host plant species vs. confamilial plant species. However, EHB-infected and EHB-free strains did not differ in their capacity to grow on or degrade fresh plant material or material from related hosts.

We evaluated the effects of two closely related EHB in the genus *Luteibacter* (Gammaproteobacteria) on substrate use, cellulase activity, ligninase activity, and plant tissue degradation by two species of foliar endophytes in the Pezizomycotina (*Pestalotiopsis* sp. 9143, Sordariomycetes; *Microdiplodia* sp. 9145, Dothideomycetes). Specifically, we test the hypotheses that the presence and identity of EHB influence endophyte growth on cellulose- or lignin-based media, the presence and/or extent of fungal cellulase or ligninase activity, and the capacity of endophytes to degrade living and senescent foliage of their host species and related trees.

Materials and Methods

As part of a previous study, focal endophytes were isolated from healthy, surface-sterilized foliage of *Platycladus orientalis* (Cupressaceae) in Durham, N.C. (Hoffman and Arnold 2010): *Pestalotiopsis* sp. 9143 with its naturally occurring bacterial symbiont, *Luteibacter* sp. 9143, and *Microdiplodia* sp. 9145, with its naturally occurring bacterial symbiont, *Luteibacter* sp. 9145. The fungi are distantly related members of the Ascomycota, representing distinct classes (Sordariomycetes and Dothideomycetes, respectively). The *Luteibacter* species are closely related; their 16S rRNA sequences are 100% identical, and whole genome sequences are nearly invariant (Baltrus et al. in prep). *Luteibacter* sp. 9143 has been shown to enhance production of indole-3-acetic acid by *Pestalotiopsis* sp. 9143 (Hoffman et al. 2013), but other aspects of their interactions, and functional aspects of the association between *Microdiploda* sp. 9145 and *Luteibacter* sp. 9145, have not been evaluated previously. Both associations are accessioned as living cultures at the Robert L. Gilbertson Mycological Herbarium at the University of Arizona (accessions MYCO-ARIZ 9143 and 9145).

We prepared eight fungal inocula from these strains: endophyte *Pestalotiopsis* sp. 9143 with *Luteibacter* sp. 9143; endophyte *Microdiplodia* sp. 9145 with *Luteibacter* sp. 9145; each endophyte growing axenically after removal of EHB via antibiotic treatments (i.e., cured strains; see below); each endophyte with its native EHB after removal and resynthesis of the association; and each endophyte after removal of EHB and cross-infection with a novel EHB (*Pestalotiopsis* sp. 9143 with *Luteibacter* sp. 9145, and *Microdiplodia* sp. 9145 with *Luteibacter* sp. 9143). We also prepared two bacterial inocula: *Luteibacter* sp. 9143 and *Luteibacter* sp. 9145, each growing axenically. Unless otherwise stated, fungal strains were maintained on 2% malt extract agar (MEA) at 25° C. and bacterial strains were grown in Luria broth (Bertani 1952) at 25° C.

To establish axenic fungal cultures, each endophyte was cured of its EHB by cultivation on 2% MEA amended with four antibiotics: ampicillin (100 µg/ml), kanamycin (50 g/ml), tetracycline (10 µg/ml), and ciprofloxacin (40 µg/ml). To resynthesize native associations and to inoculate endophytes with novel EHB, each axenic fungus was blended individually in three, 5 sec, high-speed pulses in a sterile blender (Waring 51BL31). Fungal suspensions were quantified with a spectrophotometer (OD 600) and normalized with respect to axenic bacterial inocula at a ratio of 5:1 mycelium:bacteria. The resulting mixture was co-cultured in 1×potato dextrose broth for 7 days at 27° C. in full darkness, with agitation on a rotary shaker at 100 rpm. After incubation, each co-culture was plated on 2% water agar. Bacterial infection status was verified as described below.

Molecular Analyses of EHB

Genomic DNA was extracted directly from fresh fungal mycelium collected from inside the growing edge of a fungal colony using a modified protocol from the Extract-N-Amp tissue PCR kit (Sigma-Aldrich). Mycelium was ground with a sterile pestle prior to heat lysis. Genomic DNA was screened for the presence of bacteria by 16 S rRNA PCR using RedTaq (Sigma) and primers 27F/1492 (Lane 1991). PCR conditions followed Hoffman and Arnold (2010) with the following amendments: 50° C. annealing temperature and 40 cycles. Positive and negative controls were used in every PCR.

Positive 16 S rRNA PCR products were cleaned using ExoSAP-IT (Affymetrix) and Sanger-sequenced bidirectionally at the University of Arizona Genetics Core. Sequences were assembled automatically, bases called, and quality scores assigned by phred (Ewing and Green 1998) and phrap (Ewing et al. 1998) with orchestration by Mesquite v. 1.06 (Maddison and Maddison 2011).

Consensus sequences were edited manually in Sequencher 5.1 (Gene Codes Corporation) and compared against the known sequences obtained from the same specimens by (Hoffman and Arnold 2010). In all cases, sequences were 100% identical to those of the previously studied samples. Sequences also were queried against GenBank using BLASTn (Altschul et al. 1990, Benson et al. 2014). Taxonomic placement within *Luteibacter*, validated previously by phylogenetic analysis for 9143 (Hoffman et al. 2013), was confirmed using a ≥99% match over the full sequence length. As needed, the same methods were used to confirm the identity of EHB growing axenically.

We did not identify any additional EHB or free-living bacteria in the fungal cultures used in this study. Negative PCR products (i.e., those for which no bands were evident after 16 S rRNA PCR) were cloned (Agilent, StrataClone) following the manufacturer's instructions for reactions using half volumes. No positive clones were recovered from fungi after antibiotic treatment or from negative controls.

LIVE/DEAD staining. Microscopy and staining using the LIVE/DEAD BacLight Bacterial Viability Kit (Invitrogen) was used to confirm that EHB in fungal mycelia that were positive in the 16 S assay were not present outside of fungal hyphae (i.e., were not ectosymbiotic or extrahyphal) and were viable (Hoffman and Arnold 2010). A Leica 4000 MB compound microscope with a 100-W mercury arc lamp was used for fluorescent imaging at room temperature with a Chroma Technology 35002 filter set (480-nm excitation/520-nm emission) and 100×APO oil objective.

To prepare samples for visualization, fresh hyphae were scraped from the surface of the growing edge of each colony on 2% MEA. Hyphae were placed on a glass slide with 15 µl of 1:1:18 LIVE/DEAD stain (component A: component B: $diH_2O$), covered with a coverslip, and incubated in darkness for 20 min. Sterile distilled water then was pulled through the slide mount with blotting paper. Slides were sealed with clear acrylic nail polish, which was allowed to dry before viewing. Three replicate slides were prepared per fungal culture, and in all cases, replicates from the same material were consistent. The presence of viable EHB was defined by positive PCR results and a lack of extrahyphal or ectosymbiotic bacteria (as determined by comparison with contaminated strains).

In Vitro Cellulase and Ligninase Activity Assays

For each of ten inocula (eight fungal, two bacterial), we inoculated six Petri dishes containing equal volumes of 2% MEA amended with 0.5% carboxymethylcellulose (i.e., cellulose medium; cellulase assay) or 2% water agar amended with 0.05% indulin (i.e., lignin medium; ligninase assay) following Gazis et al. (2012). Each fungal inoculum consisted of a 6 mm plug of actively growing mycelium, which was placed on the assay plate with the mycelial surface in contact with the medium. Each inoculum for axenic bacteria consisted of a transfer by sterile loop from a three-day-old colony on 2% MEA. Inoculated plates were incubated at 22° C. in darkness for 10 day (fungal inocula) or three day (axenic bacterial inocula). Colony diameter was then was measured with a ruler. Measurements were taken on two perpendicular axes that intersected at the colony center, and were averaged to yield the final diameter value.

To evaluate clearing of the medium due to enzyme activity (i.e., to quantify enzyme activity), hyphae were scraped from the surface of the plate with a rubber policeman and sterile water. Plates then were flooded with a 0.2% w/v Congo red solution (cellulase assay) or a 1.0% w/v $FeCl_3$ and $K_3$ [Fe(CN)]$_6$ solution (ligninase assay), incubated at room temperature for 40 min, and washed several times with 1M NaCl (Gazis et al. 2012).

Clearing of the medium either beneath colonies or beyond the growing edges provided evidence of enzyme activity. If present, the extent of activity was evaluated by measuring the zone of clearing beyond the colony edge. The zone of clearing was measured with a ruler on two perpendicular axes as above.

The presence and extent of enzyme activity was evaluated twice for each fungus with its native bacterial associate and when grown axenically. These assays were conducted once for the resynthesized associations and novel associations, and for the bacteria growing axenically. Presence/absence of activity was consistent across all replicates for each inoculum in each trial, and did not differ by trial when trials were replicated. Here we focus on the second trial because the first trial did not include all inoculum types, results of the first and second trials were qualitatively consistent, and because the first trial was conducted at a lower temperature (22° C.), resulting in less growth than was observed in the second trial.

Statistical Analyses for Growth and Enzyme Assays

Colony diameter for each fungal inoculum type was compared within each assay type to determine effects of EHB presence and identity on fungal growth and enzyme activity. Diameter values were normally distributed and were compared with ANOVA, followed by post-hoc Student's t-tests. A Bonferroni-adjusted alpha level of 0.0083 was used for each post-hoc test. Colony diameters for axenic bacteria were obtained on cellulase assay plates, but these bacteria did not grow on ligninase assay plates. Their diameter values on cellulase assay plates were normally distributed and were compared (i.e., 9143 vs. 9145) using a t-test.

The extent of clearing for each fungal inoculum was scaled by colony diameter prior to analysis. Values were then compared to determine effects of EHB presence and identity. Because enzyme activity values were not normally distributed, means were compared using a Kruskal-Wallis test, followed by post-hoc Mann-Whitney tests. A Bonferroni-adjusted alpha level of 0.0083 was used for each post-hoc test. No clearing of the medium was observed beyond the colony edge for the axenic bacteria on cellulase assay plates. All analyses were carried out in JMP v. 11.0.0 (SAS Institute, Cary, N.C., USA).

In Vitro Mass-Loss Experiments

Fresh (i.e., living, asymptomatic, and green) and dry (i.e., senescent, asymptomatic, and brown) leaf material was collected from three individuals of each of three species of Cupressaceae (*Platycladus orientalis, Cupressus arizonica* and *Juniperus deppeana*) at the University of Arizona Campus Arboretum. Leaf material was collected in late spring to early summer from branches ca. 1.5 m above ground. All trees were apparently healthy and were cultivated in a park-like setting with supplemental water.

Two mass-loss experiments were conducted. In the first preliminary experiment, we focused on seven endophyte/EHB associations, with inocula prepared as above but including only the native association and axenic fungus in each case: *Pestalotiopsis* sp. 9143 with *Luteibacter* sp. 9143; *Microdiploda* sp. 9145 with *Luteibacter* sp. 9145; *Cladosporium* sp. 9128 with *Curtobacterium* sp. 9128, *Alternaria* sp. 9055 with *Sphingomonas* sp. 9055, *Microdiplodia* sp. 9145 with *Erwinia* sp. 9145, *Microdiplodia* sp. 9140 with *Pantoea* sp. 9140, and *Microdiplodia* sp. 9140 with *Rhizobium* sp. 9140. These associations were isolated from *Platycladus orientalis* in a previous study (Hoffman and Arnold 2010) and are accessioned at the Robert L. Gilbertson Mycological Herbarium at the University of Arizona (accessions MYCO-ARIZ 9128, MYCO-ARIZ 9140, MYCO-ARIZ 9143, MYCO-ARIZ 9145, MYCO-ARIZ 9055). We evaluated the mass loss of green and senescent tissues of three species of Cupressaceae, listed above.

In the second experiment, we focused only on *Pestalotiopsis* sp. 9143 and *Microdiplodia* sp. 9145. We used the eight fungal inocula described above, including axenic, native, resynthesized, and cross-infected associations, and considered green and senescent tissues of three species of Cupressaceae, listed above.

In each experiment, leaf samples were washed in tap water and placed in 0.5 g amounts into individual, sterile 100 mm Petri plates. Three plates (experiment 1) or six plates (experiment 2) were prepared per tissue type and sample for each inoculum type. Each leaf sample was surface-sterilized by flooding with 95% EtOH (10 sec) followed by 0.53% NaOCl (2 min), and 70% EtOH for (2 min) (Arnold and Lutzoni 2007). Each sample then was inoculated with 3 mL of sterile water and 75 uL of fungal inoculum prepared by grinding a 6 mm plug of actively growing mycelium on 2% MEA in 1 mL sterile water. Control treatments consisted of a 6 mm plug of sterile medium ground in 1 mL of sterile water. To evaluate whether fungi present in leaf tissue prior to inoculation could influence our results, an additional trial was included in which samples of dry material from *P. orientalis* were collected and autoclaved (1.2 bar, 20 min) after surface-sterilization to inactivate endogenous endophytes.

Plates were wrapped three times with Parafilm, weighed immediately, and then incubated at room temperature with approximately 12 h light/dark cycles. Plates were weighed weekly for 6 weeks. At the end of the experiment, fungal growth was scored visually on a scale from 0 to 4 (0=no visible growth, 1=1-25% coverage, 2=26-50% coverage, 3=51-75% coverage and 4=76-100% coverage of available leaf material by fungal mycelium). Mass loss was calculated as the difference in mass of each sample after 6 weeks relative to the original mass, scaled by original weight. Mass was predicted to leave each sample in the form of carbon dioxide due to aerobic respiration and to a lesser extent, water vapor. For each fungal inoculum, mean scaled mass loss was compared by ANOVA to determine the effects of EHB presence and identity, followed by post-hoc Student's t-tests with a Bonferroni-adjusted alpha level of 0.0083. All analyses were carried out in JMP v. 11.0.0 (SAS Institute, Cary, N.C., USA).

Results

Growth on Cellulase Assay Plates

All fungal inocula, and both axenic bacteria, grew successfully on cellulase assay plates. For both *Pestalotiopsis* sp. 9143 and *Microdiplodia* sp. 9145, colony diameter on that medium was not influenced significantly by the presence or absence of EHB (FIG. 2). For each fungal species, colony diameter on cellulase assay plates did not differ between resynthesized associations (i.e., the fungus and its native EHB reassociated after curing) and native associations with EHB.

However, as shown in FIG. 2, growth of both fungal strains was influenced by the identity of EHB. Growth of *Pestalotiopsis* sp. 9143 was significantly reduced when infected by *Luteibacter* sp. 9145 relative to infection by *Luteibacter* sp. 9143 or axenic growth. Growth of *Microdiplodia* sp. 9145 was significantly increased when infected by *Luteibacter* sp. 9143 relative to infection by *Luteibacter* sp. 9145 or axenic growth. In both cases, fungi infected with *Luteibacter* sp. 9143 grew more than conspecific fungal strains infected with *Luteibacter* sp. 9145. The growth of axenic bacteria was similar between the two bacterial species.

Growth on Ligninase Assay Plates

All fungal inocula grew successfully on ligninase assay plates, as shown in Table 2 and Table 3. Neither axenic bacterium grew on this medium.

TABLE 2

| Fungus | Bacterium | Status | Growth Cellulase medium | Growth Ligninase medium | Activity Cellulase activity | Activity Ligninase activity |
|---|---|---|---|---|---|---|
| Pestalotiopsis sp. 9143 | Luteibacter sp. 9143 | Naturally infected | Yes | Yes | Yes$^A$ | Yes$^A$ |
| Pestalotiopsis sp. 9143 | Luteibacter sp. 9143 | Resynthesized | Yes | Yes | Yes$^A$ | Yes$^A$ |
| Pestalotiopsis sp. 9143 | Luteibacter sp. 9145 | Cross-infected | Yes | Yes | Yes$^A$ | No |
| Pestalotiopsis sp. 9143 | None | Axenic fungus | Yes | Yes | No | Yes$^A$ |
| Microdiplodia sp. 9145 | Luteibacter sp. 9145 | Naturally infected | Yes | Yes | Yes$^a$ | No |
| Microdiplodia sp. 9145 | Luteibacter sp. 9145 | Resynthesized | Yes | Yes | Yes$^a$ | No |
| Microdiplodia sp. 9145 | Luteibacter sp. 9143 | Cross-infected | Yes | Yes | Yes$^a$ | No |
| Microdiplodia sp. 9145 | None | Axenic fungus | Yes | Yes | No | Yes |
| None | Luteibacter sp. 9143 | Axenic bacterium | Yes | No | Yes$^1$ | N/A |
| None | Luteibacter sp. 9145 | Axenic bacterium | Yes | No | Yes$^1$ | N/A |

TABLE 3

| Fungus | Bacterium | Status | Cellulase activity Mean ± SD | Ligninase activity Mean ± SD |
|---|---|---|---|---|
| Pestalotiopsis sp. 9143 | Luteibacter sp. 9143 | Naturally infected | 1.02 ± 0.03 | 1.06 ± 0.01 |
| Pestalotiopsis sp. 9143 | Luteibacter sp. 9143 | Re-synthesized | 1.01 ± 0.01 | 1.01 ± 0.03 |
| Pestalotiopsis sp. 9143 | Luteibacter sp. 9145 | Cross-infected | 1.00 ± 0.00 | 0.00 ± 0.00 |
| Pestalotiopsis sp. 9143 | None | Axenic fungus | 0.00 ± 0.00 | 1.02 ± 0.03 |
| Microdiplodia sp. 9145 | Luteibacter sp. 9145 | Naturally infected | 1.04 ± 0.02 | 0.00 ± 0.00 |
| Microdiplodia sp. 9145 | Luteibacter sp. 9145 | Re-synthesized | 1.03 ± 0.01 | 0.00 ± 0.00 |
| Microdiplodia sp. 9145 | Luteibacter sp. 9143 | Cross-infected | 1.03 ± 0.01 | 0.00 ± 0.00 |
| Microdiplodia sp. 9145 | None | Axenic fungus | 0.00 ± 0.00 | 1.14 ± 0.06 |
| None | Luteibacter sp. 9143 | Axenic bacterium | 1.00 ± 0.00 | N/A |
| None | Luteibacter sp. 9145 | Axenic bacterium | 1.00 ± 0.00 | N/A |

Table 2 and Table 3 show the effects of endohyphal bacteria (EHB) on fungal growth on enzyme assay plates and the presence/absence of cellulase and ligninase activity. Columns indicate the identity of fungi, the identity of bacteria, the status of each culture, and the presence/absence of growth and activity observed on cellulase and ligninase assay plates. In Table 3, columns further indicate the means and standard deviations of the normalized zones of clearing observed on cellulase and ligninase assay plates. In Table 2, 'Yes' for growth indicates that growth was observed; quantitative results are presented in Table 3 and in FIG. 2 and FIG. 3. 'Yes' for activity indicates observed clearing of the medium; quantitative results are presented in Table 3. Within each panel, superscripts within columns are the same if quantitative results for active strains did not differ significantly. The last two rows indicate results for axenic bacterial cultures.

For both *Pestalotiopsis* sp. 9143 and *Microdiplodia* sp. 9145, colony diameter on indulin medium was not influenced by the presence vs. absence of EHB, nor by EHB identity. For each fungal species, colony diameter was greater in the resynthesized association (i.e., the fungus and its native EHB re-associated after curing) and after curing and cross-inoculation with the non-native bacterium, relative to the native associations or when growing axenically. Within each fungal species, growth was similar between the resynthesized and the inoculated strains regardless of the identity or novelty of the EHB.

Presence/Absence of Cellulase Activity

The presence of EHB influenced cellulase activity. For *Pestalotiopsis* sp. 9143, clearing of the cellulose medium was observed for all fungal inocula containing EHB, but not when the fungus was grown axenically. The same result was obtained for *Microdiplodia* sp. 9145. The cellulose medium was also cleared by both bacteria when grown axenically.

Quantification of Cellulase Activity

For *Pestalotiopsis* sp. 9143, the identity of EHB did not significantly influence the extent of clearing beyond colony edges on cellulose medium. Clearing was consistent when the fungus was infected natively with *Luteibacter* sp. 9143, resynthesized after curing, or infected by *Luteibacter* sp. 9145. Similarly, for *Microdiplodia* sp. 9145, the identity of EHB did not significantly influence the zone of clearing beyond colony edges on cellulose medium.

Presence/Absence of Ligninase Activity

For *Pestalotiopsis* sp. 9143, clearing of the indulin medium was observed for all fungal inocula except that containing *Luteibacter* sp. 9145, indicating an effect of EHB identity and an intrinsic capacity of the fungus to clear the indulin medium when growing axenically. Clearing was only observed for *Microdiplodia* sp. 9145 when it was grown axenically: the presence of EHB was associated with a loss of ligninase activity. As mentioned above, both axenic bacteria failed to grow on the indulin medium.

Quantification of Ligninase Activity

For *Pestalotiopsis* sp. 9143, the identity of EHB significantly influenced the zone of clearing beyond colony edges. Clearing was significantly greater when the fungus was infected with its native bacterium (*Luteibacter* sp. 9143, either naturally or through curing and resynthesis), or when grown axenically, than when it carried *Luteibacter* sp. 9145 (for which no clearing was observed outside the colony edge). Clearing by the fungus with *Luteibacter* sp. 9143 did not differ significantly from clearing by the fungus when grown axenically.

For *Microdiplodia* sp. 9145, the presence of EHB prevented clearing beyond colony edges while the axenic strain displayed significantly more clearing. No zone of clearing was observed when fungal inocula contained EHB, and the identity of the EHB did not influence clearing of the medium.

In Vitro Mass Loss Experiment 1

When results for seven fungal strains were considered together, the percent of mass lost during the experiment from green foliage of *P. orientalis* did not differ as a function of the presence or absence of EHB in fungal inocula (FIG. 4). Similarly, EHB did not influence mass loss from green foliage of *J. deppeana* or *C. arizonica*, nor from senescent tissue of those species (FIG. 1). However, the presence of EHB in fungal inocula led to significantly greater mass loss from senescent foliage of *P. orientalis* compared to fungi without EHB (FIG. 4).

In Vitro Mass Loss Experiment 2

In the second mass-loss experiment, no significant difference was observed in the percent of mass lost from fresh material of *P. orientalis* as a function of EHB presence or identity (FIG. 5A, *Pestalotiopsis*; FIG. 5B, *Microdiplodia*). However, mass loss differed significantly in senescent tissue of *P. orientalis* as a function of EHB treatment within each fungal host. Significantly more mass was lost from senescent foliage treated with *Pestalotiopsis* sp. 9143 with its native bacterium than when treated by the axenic fungus (FIG. 5C). Mass loss due to the resynthesized association did not differ significantly from treatment with the native association (FIG. 5C). The presence of *Luteibacter* sp. 9145 led to a decrease in mass loss relative to the same fungus containing *Luteibacter* sp. 9143 (FIG. 5C).

Mass loss differed significantly in senescent tissue of *P. orientalis* treated with *Microdiplodia* as a function of EHB presence, but not identity (FIG. 5D). Mass loss was significantly greater when *Microdiplodia* contained EHB vs. treatment by the axenic fungus (FIG. 5D). There was no difference in mass loss among *Microdiplodia* strains with the native bacterium, following resynthesis with *Luteibacter* sp. 9145, or following cross-infection with *Luteibacter* sp. 9143.

Mass loss was consistent for both fungi when they contained *Luteibacter* sp. 9143, but not when they contained *Luteibacter* sp. 9145. In that case, mass loss was greater in the native association than in the cross-infected association (FIGS. 5C and 5D; t=5.250, df=9, P=0.0005). Results were consistent when *P. orientalis* tissue was autoclaved prior to the experiment (results not shown).

Each plate was scored visually for hyphal coverage at the end of the experiment. Mass loss was positively related to the prevalence of hyphal coverage.

Here we examined the influence of EHB on foliar fungi with a focus on substrate use, enzyme activity, and the ability to degrade plant material. We focused specifically on cellulase and ligninase activity because of the central importance of such enzymes to plant cell wall decomposition and their applications in biofuel production and related industries. Our study is the first to evaluate how EHB influence enzymatic activity of fungi. Our work reveals the previously overlooked importance of these bacterial endosymbionts in cellulase and ligninase activity and plant decomposition. Moreover, we show that particular bacteria have distinctive phenotypic effects, which differ as a function of the fungus that they inhabit.

An important aspect of this work was the establishment of protocols for curing fungal strains of their EHB, reintroducing EHB to those cured cultures, and exchanging EHB among fungal taxa. Here, we showed that *Luteibacter* strains could be transferred to establish new symbioses with novel fungal hosts in a different class of Ascomycota. Moreover, we showed that two EHB strains that were 100% identical in their 16S rRNA had different effects on their original and novel hosts. In general, bacterial-fungal associations that were generated by resynthesis were very similar in phenotype to original associations (but see ligninase results, above).

Substrate Use

Using in vitro assays, we found that EHB influenced the ability of focal fungi to use cellulose- and lignin-based substrates. Although growth on the cellulase assay medium did not differ as a function of the presence and absence of EHB, the identity of the bacterial strain resulted in differences in growth on that medium. In those assays, inoculation with *Luteibacter* sp. 9143 always yielded greater growth than inoculation with *Luteibacter* sp. 9145.

In growth assays on the ligninase assay medium, the capacity of fungi to grow was not influenced by presence, absence, or identity of EHB. Resynthesized and cross-infected strains grew more than did strains with the native infection, and resynthesis is most effective on low-nutrient conditions. The absence of malt extract in the ligninase assay medium resulted in it having a lower nutrient composition than the cellulase assay medium. This may lead to enhanced fungal growth when nutrients are limiting due to EHB presence, particularly if the bacterial titer is increased by the resynthesis process. In future work we will test the hypothesis that the greater growth of resynthesized strains on ligninase assay plates may reflect an increased bacterial titer relative to naturally infected strains. We have observed the loss of EHB from fungal cultures having been repeatedly subcultured or in long-term storage (Hoffman et al. 2013), potentially contributing to a disparity in titer levels between recultured, native associations and newly resynthesized associations.

EHB can Alter Fungal Enzyme Activity

EHB can alter cellulase and ligninase activity of foliar fungi in vitro. Enzyme activity may be altered by presence of EHB (cellulase) or determined by the genotype of the symbionts (ligninase). The increase of fungal cellulase activity as a result of bacterial infection may be due to enzyme production by the bacterium, or an increased activity due to the symbiosis. Axenic *Luteibacter* sp. 9143 and 9145 grew on cellulase medium plates, and exhibited cellulase activity under the bacterial colonies. However, neither of the bacteria grew on ligninase medium plates. Thus, fungal ligninase activity may be associated with a change in fungal growth as a result of EHB identity, rather than production of ligninase enzymes by the bacteria themselves.

In general, we observed that when bacterial treatment affected fungal growth on one medium, we saw no change or a change in growth in the same direction on the other medium. The exception was *Pestalotiopis* sp. 9143 inoculated with *Luteibacter* sp. 9145, which grew less on cellulase medium and more on liginase medium relative to the axenic fungus or the natural association. *Pestalotiopis* sp. 9143 with *Luteibacter* sp. 9145 demonstrated cellulase activity but not ligninase activity, and thus differed in both assays from the axenic fungus and the natural association. Because the pattern differed in *Microplodia*, our results can be taken to suggest that specific associations, and novelty of interactions, can be powerful in shaping the outcome of enzyme activity.

EHB Increased Fungal Degradation of Leaf Litter

In two experiments, EHB increased fungal degradation of, and fungal growth on, senescent foliage of the host species from which fungi were originally isolated (*P. orientalis*). However, EHB did not influence degradation of leaf litter from other confamilial trees, nor living material from any host species. In future work we will evaluate the hypothesis that specific signals produced in living foliar tissue or at the onset of plant tissue death influence fungal/bacterial growth and activity.

In *Pestalotiopsis*, we observed greater mass loss when associations demonstrated both ligninase and cellulase activity (vs. only ligninase or only cellulase activity). Each *Microdiplodia* inoculum was only active in one enzyme, but in that species the presence or degree of cellulase activity was the more important indicator of potential mass loss.

Conclusions. Together, our results reveal that EHB can influence enzymatic activity and plant biomass degradation by fungal endophytes.

Thus, described herein are methods for transferring endohyphal bacterium from a first endophytic fungus to a second endophytic fungus comprising the following steps: preparing a bacterial inoculum of the endohyphal bacterium from the first endophytic fungus, and inoculating the second endophytic fungus with the bacterial inoculum. In more specific embodiments, the methods comprises using first and second endophytic fungi of same species and strain. In other more specific embodiments, the first and second endophytic fungi are of different strains of the same species. In yet other more specific embodiments, the first and second endophytic fungi are of different species.

Also described are methods for transferring endohyphal bacterium from a first endophytic fungus to a second endophytic fungus comprising the following steps: preparing a bacterial inoculum of the endohyphal bacterium from the first endophytic fungus, and inoculating the second endophytic fungus with the bacterial inoculum, and wherein the first and second endohyphal bacteria are of the same species, or are of different strains of the same species, or are of different species.

Also described herein are methods for transferring endohyphal bacteria between a first endophytic fungus and a second endophytic fungus comprising the following steps: preparing a first bacterial inoculum of the endohyphal bacterium from the first fungus, preparing a second bacterial inoculum of the endohyphal bacterium from the second fungus, and cross-inoculating the fungi by inoculating the first fungus with the second bacterial inoculum and inoculating the second fungus with the first bacterial inoculum.

Also described herein are methods for examining phenotypic changes in an endophytic fungi of the phylum Ascomyota comprising treating the endophytic fungi with an antibiotic to cure the fungi of its endohyphal bacteria, and comparing phenotypic activity of the fungi before and after treatment with the antibiotic. In more specific embodiments, the method comprises inoculating the cured fungi with endohyphal bacteria to resynthesize the fungi with endohyphal bacteria symbiont, and comparing the phenotypic activity of the cured fungi to the resynthesized fungi.

Also described herein are methods for altering the enzymatic activity of endophytic fungi, comprising transferring endohyphal bacteria from a first endophytic fungus to a second endophytic fungus. In more specific embodiments of this method, the enzymatic activity is increased, or decreased, or is lignocellulytic activity. In yet other embodiments, the fungus is *Pestalotiopsis* and the bacterium is *Luteibacter*, or the fungus is *Microdiplodia* and the bacterium is *Luteibacter*. In a specific embodiment, the method involves the enzymatic activity of degrading plant material.

Also described herein is a method for increasing degradation of plant material comprising increasing enzymatic activity of endophytic fungi in the plant material.

References cited in the application are listed below.

Alexopoulos C J, Mims C W, Blackwell M. 1996. Introductory Mycology, 4th ed. New York: Wiley.

Altschul S F, Gish W, Miller W, Myers E W and Lipman D J. 1990. Basic local alignment search tool. Journal of Molecular Biology. 215:403-410.

Arnold A E. 2007. Understanding the diversity of foliar endophytic fungi: progress, challenges, and frontiers. Fungal Biology Reviews. 21:51-66.

Arnold A E, Lutzoni F. 2007. Diversity and host range of foliar fungal endophytes: Are tropical leaves biodiversity hotspots? Ecology. 88:541-549.

Arnold A E, Mejia L C, Kyllo D, Rojas E I, Maynard Z, Robbins N, Herre E A. 2003. Fungal endophytes limit pathogen damage in a tropical tree. Proceedings of the National Academy of Sciences of the United States of America. 100:15649-15654.

Augé R M. 2001. Water relations, drought and vesicular-arbuscular mycorrhizal symbiosis. Mycorrhiza. 11:3-42.

Bacon C W. 1993. Abiotic stress tolerances (moisture, nutrients) and photosynthesis in endophyte-infected tall fescue. Agriculture, Ecosystems & Environment. 44:123-141.

Bagchi R, Gallery R E, Gripenberg S, Gurr S J, Narayan L, Addis C E, Freckleton R P, Lewis O T. 2014. Pathogens and insect herbivores drive rainforest plant diversity and composition. Nature. 506:85-88.

Be'er A, Zhang H P, Florin E-L, Payne S M, Ben-Jacob E, Swinney H L. 2009. Deadly competition between sibling bacterial colonies. Proceedings of the National Academy of Sciences. 106: 428-433.

Benson D A, Clark K, Karsch-Mizrachi I, Lipman D J, Ostell J, Sayers E W. 2014. GenBank. Nucleic Acids Research. 42:D32-D37.

Berg G, Grube M, Schloter M, Smalla K. 2014a. The plant microbiome and its importance for plant and human health. Frontiers in Microbiology. 5.

Berg G, Grube M, Schloter M, Smalla K. 2014b. Unraveling the plant microbiome: looking back and future perspectives. Frontiers in Microbiology. 5:148.

Bertani G. 1952. Studies on lysogenesis: The mode of phage liberation by lysogenic *Escherichia coli*. Journal of Bacteriology. 62:293-300.

Bertaux J, Schmid M, Hutzler P, Hartmann A, Garbaye J, Frey-Klett P. 2005. Occurrence and distribution of endobacteria in the plant-associated mycelium of the ectomycorrhizal fungus *Laccaria* bicolor S238N. Environmental Microbiology. 7:1786-1795.

Bertaux J, Schmid M, Prevost-Boure N C, Churin J L, Hartmann A, Garbaye J, Frey-Klett P. 2003. In situ identification of intracellular bacteria related to *Paenibacillus* spp. in the mycelium of the ectomycorrhizal fungus *Laccaria* bicolor S238N. Applied and Environmental Microbiology. 69:4243-4248.

Bianciotto V, Genre A, Jargeat P, Lumini E, Becard G, Bonfante P. 2004. Vertical transmission of endobacteria in the arbuscular mycorrhizal fungus *Gigaspora margarita* through generation of vegetative spores. Applied and Environmental Microbiology. 70:3600-608.

Bianciotto V, Lumini E, Bonfante P, Vandamme P. 2003. 'Candidatus Glomeribacter gigasporarum' gen. nov., sp nov., an endosymbiont of arbuscular mycorrhizal fungi. International Journal of Systematic and Evolutionary Microbiology. 53:121-124.

Blackwell M. 2011. The fungi: 1, 2, 3 . . . 5.1 million species? American Journal of Botany. 98: 426-38.

Brian P W and Hemming F I G. 1947. Production of antifungal and antibacterial substances by fungi; preliminary examination of 166 strains of fungi imperfecti. Journal of General Microbiology. 1:158-67.

Brodey C L, Rainey P B, Tester M. 1991. Bacterial blotch disease of the cultivated mushroom is caused by an ion channel forming lipodepsipeptide toxin. Molecular Plant-Microbe Interactions. 4:407-411.

Carroll G. 1988. Fungal Endophytes in Stems and Leaves: From Latent Pathogen to Mutualistic Symbiont. Ecology. 69:2.

Carroll G. 1995. Forest endophytes: Pattern and process. Canadian Journal of Botany. 73:S1316-S1324.

Clay K, Hardy T N, Hammond A M Jr. 1985. Fungal endophytes of grasses and their effects on an insect herbivore. Oecologia. 66:1-5.

Daskin J H, Alford R A. 2012. Context-dependent symbioses and their potential roles in wildlife diseases. Proceedings of the Royal Society B: Biological Sciences 279: 1457-1465.

Denison. RF and Kiers E T. 2011. Life histories of symbiotic rhizobia and mycorrhizal fungi. Current Biology. 21:775-785.

Desiro A, Faccio A, Kaech A, Bidartondo M I, Bonfante P. 2014a. Endogone, one of the oldest plant-associated fungi, host unique Mollicutes-related endobacteria. New Phytologist. Advanced online publication. doi:10.1111/nph. 13136.

Desiro A, Salvioli A, Ngonkeu E L, Mondo S J, Epis S, Faccio A, Kaech A, Pawlowska T E, Bonfante P. 2014b. Detection of a novel intracellular microbiome hosted in arbuscular mycorrhizal fungi. ISME Journal. 8:257-270.

Eastwood D C, Floudas D, Binder M, Majcherczyk A, Schneider P, Aerts A, Asiegbu F O, Baker S E, Barry K, Bendiksby M, Blumentritt M, Coutinho P M, Cullen D, de Vries R P, Gathman A, Goodell B, Henrissat B, Ihrmark K, Kauserud H, Kohler A, LaButti K, Lapidus A, Lavin J L, Lee Y-H, Lindquist E, Lilly W, Lucas S, Morin E, Murat C, et al. 2011. The plant cell wall-decomposing machinery underlies the functional diversity of forest fungi. Science. 333:762-765.

Ewing B, Green P. 1998. Basecalling of automated sequencer traces using phred: Error probabilities. Genome Research. 8:186-194.

Ewing B, Hiller L, Wendl M, Green P. 1998. Basecalling of automated sequencer traces using phred: Accuracy assessment. Genome Research. 8:175-185.

Fisher P J. 1996. Survival and spread of the endophyte *Stagonospora pteridiicola* in *Pteridium aquilinum*, other ferns and some flowering plants. New Phytologist. 132: 119-122.

Fisher P J, Petrini O. 1992. Fungal saprobes and pathogens as endophytes of rice (*Oryza sativa* L.). New Phytologist. 120:137-143.

Frey-Klett P, Burlinson P, Deveau A, Barret M, Tarkka M, Sarniguet A. 2011. Bacterial-Fungal Interactions: Hyphens between Agricultural, Clinical, Environmental, and Food Microbiologists. Microbiology and Molecular Biology Reviews. 75: 583-609.

Fröhlich, J, Hyde K D. 1999. Biodiversity of palm fungi in the tropics: Are global fungal diversity estimates realistic? Biodiversity and Conservation. 8: 977-1004.

Gamboa M A, Bayman P. 2001. Communities of endophytic fungi in leaves of a tropical timber tree (*Guarea guidonia*: Meliaceae). Biotropica. 33:352-360.

Gazis R., Miadlikowska J., Arnold A. E., Lutzoni F., Chaverri P. 2012. Culture-based study of endophytes associated with rubber trees in Peru reveals a new class of Pezizomycotina (Xylonomycetes). *Molecular Phylogenetics and Evolution* 65(1): 294-304.

Ghignone S, Salvioli A, Anca I, Lumini E, Ortu G, Petiti L, Cruveiller S, Bianciotto V, Piffanelli P, Lanfranco L, Bonfante P. 2012. The genome of the obligate endobacterium of an A M fungus reveals an interphylum network of nutritional interactions. ISME Journal. 6:136-145.

Gilbert G S, Webb C O. 2007. Phylogenetic signal in plant pathogen-host range. Proceedings of the National Academy of Sciences of the United States of America. 104:4979-4983.

Higgins K L, Arnold A E, Coley P D, Kursar T A. 2014. Communities of fungal endophytes in tropical forest grasses: highly diverse host- and habitat generalists characterized by strong spatial structure. Fungal Ecology. 8:1-11.

Hoffman M. 2010. Bacterial endosymbionts of endophytic fungi: diversity, phylogenetic structure, and biotic interactions (Doctoral dissertation). Retrieved from ProQuest Dissertations and Theses. Order No. 3402061.

Hoffman, M. and A. E. Arnold. 2010. Diverse bacteria inhabit living hyphae of phylogenetically diverse fungal endophytes. *Applied and Environmental Microbiology* 76: 4063-4075.

Hoffman M T, Gunatilaka M K, Wij eratne K, Gunatilaka L, Arnold A E. 2013. Endohyphal bacterium enhances production of indole-3-acetic acid by a foliar fungal endophyte. PLoS ONE. 8:e73132.

Hogan D A, Kolter R. 2002. *Pseudomonas-Candida* interactions: an ecological role for virulence factors. Science. 296:2229-2232.

Izumi H, Anderson I C, Alexander I J, Killham K, Moore E. 2006. Endobacteria in some ectomycorrhiza of Scots pine (*Pinus sylvestris*). FEMS Microbiology Ecology. 56:34-43.

Jankowska A. Laubitz D, Antushevich H, Zabielski R, Grzesiuk E. 2008. Competition of *Lactobacillus paracasei* with *Salmonella enterica* for adhesion to caco-2 cells. Journal of Biomedicine and Biotechnology. 2008:357964.

Lackner G, Moebius N, Hertweck C. 2011. Endofungal bacterium controls its host by an hrp type III secretion system. ISME Journal. 5:252-261.

Lane D J. 1991. 16S/23S rRNA sequencing. In: E. Stackebrandt and M. Goodfellow. Nucleic acid techniques in bacterial systematics. New York, N.Y.: John Wiley & Sons, Inc. pp. 115-176.

Lenski R E, Rose M R, Simpson S C, Tadler S C. 1991. Long-Term experimental evolution in *Escherichia coli*. I. Adaptation and divergence during 2,000 generations. The American Naturalist. 138:1315-1341.

Lewis G C. 2004. Effects of biotic and abiotic stress on the growth of three genotypes of *Lolium perenne* with and without infection by the fungal endophyteNeotyphodium *lolii*. Annals of Applied Biology. 144:53-63.

Lindow S E, Brandl M T. 2003. Microbiology of the phyllosphere. Applied and Environmental Microbiology. 69:1875-1883.

Lodge D J, Fisher P J, Sutton B C. 1996. Endophytic fungi of *Manilkara bidentata* leaves in Puerto Rico. Mycologia. 88:733-738.

Lumini E, Bianciotto V, Jargeat P, Novero M, Salvioli A, Faccio A, Becard G, Bonfante P. 2007. Presymbiotic growth and sporal morphology are affected in the arbuscular mycorrhizal fungus *Gigaspora margarita* cured of its endobacteria. Cellular Microbiology. 9:1716-1729.

MacDonald R M, Chandler M R. 1981. Bacterium-like organelles in the vesicular-arbuscular mycorrhizal fungus *Glomus caledonius*. New Phytologist. 89:241-246.

Maddison W P, Maddison D R. 2011. Mesquite: A modular system for evolutionary analysis. mesquiteproject.org.

Malinowski D P, Belesky D P. 2000. Adaptations of endophyte-infected cool-season grasses to environmental stresses: mechanisms of drought and mineral stress tolerance. Crop Science. 40:923-940.

Marschner H, Dell B. 1994. Nutrient uptake in mycorrhizal symbiosis. Plant Soil. 159:89-102.

Mejia L C, Rojas E I, Maynard Z, Bael S V, Arnold A E, Hebbar P, Samuels G J, Robbins N, Herre E A. 2008. Endophytic fungi as biocontrol agents of *Theobroma cacao* pathogens. Biological Control. 46:4-14.

Minerdi D, Bossi S, Maffei M E, Gullino M L, Garibaldi A. 2011. *Fusarium oxysporum* and its bacterial consortium promote lettuce growth and expansin A5 gene expression through microbial volatile organic compound (MVOC) emission. FEMS Microbiology Ecology. 76:342-351.

Minerdi D, Moretti M, Gilardi G, Barberio C, Gullino M L, Garibaldi A. 2008. Bacterial ectosymbionts and virulence silencing in a *Fusarium oxysporum* strain. Environmental Microbiology. 10:1725-1741.

Márquez L M, Redman R S, Rodriguez R J, Roossnick M J. 2007. A virus in a fungus in a plant: three-way symbiosis required for thermal tolerance. Science. 315:513-515.

McCreadie J W, Beard C E, Adler P H. 2005. Context-dependent symbiosis between black flies (Diptera: Simuliidae) and Trichomycete fungi (Harpellales: Legeriomycetaceae). Oikos. 108:362-370.

Moebius N, Üzüim Z, Dijksterhuis J, Lackner G, Hertweck C. 2014. Active invasion of bacteria into living fungal cells. eLIFE. 3:e03007.

Mondo S J, Toomer K H, Morton J B, Lekberg Y, Pawlowska T E. 2012. Evolutionary stability in a 400-million-year-old heritable facultative mutualism. Evolution. 66:2564-2576.

Naumann M, Schuessler A, Bonfante P. 2010. The obligate endobacteria of arbuscular mycorrhizal fungi are ancient heritable components related to the Mollicutes. ISME Journal. 4:862-871.

Partida-Martinez L P, Groth I, Schmitt I, Richter W, Roth M, Hertweck C. 2007a. *Burkholderia rhizoxinica* sp. nov and *Burkholderia endofungorum* sp. nov., bacterial endosymbionts of the plant-pathogenic fungus *Rhizopus microsporus*. International Journal of Systematic and Evolutionary Microbiology. 57:2583-2590.

Partida-Martinez L P, Monajembashi S, Greulich K-O, Hertweck C. 2007b. Endosymbiont-dependent host reproduction maintains bacterial-fungal mutualism. Current Biology. 17:773-777.

Petrini O. 1991. Fungal endophytes of tree leaves. In: Microbial Ecology of Leaves. New York, N.Y.: Springer New York. pp. 179-197.

Photita W, Lumyong S, Lumyong P. 2004. Are some endophytes of *Musa acuminata* latent pathogens. Fungal Diversity. 16:130-140.

Picard K T, Letcher P M, Powell M J. 2013. Evidence for a facultative mutualist nutritional relationship between the green coccoid alga *Bracteacoccus* sp. (Chlorophyceae) and the zoosporic fungus *Rhizidium phycophilum* (Chytridiomycota). Fungal Biology. 117:319-28.

Promputtha I, Hyde K D, McKenzie E H C, Peberdy J F, Lumyong S. 2010. Can leaf degrading enzymes provide evidence that endophytic fungi becoming saprobes? Fungal Diversity. 41:89-99.

Promputtha I, Lumyong S, Dhanasekaran V, McKenzie E H C, Hyde K D, Jeewon R. 2007. A Phylogenetic Evaluation of Whether Endophytes Become Saprotrophs at Host Senescence. Microbial Ecology. 53:579-590.

Rai A N, Rowell P, Stewart W D P. 1983. Interactions between cyanobacterium and fungus during 15N2-incorporation and metabolism in the lichen *Peltigera canina*. Archives of Microbiology. 134:136-142.

Rodrigues F K. 1994. The foliar fungal endophytes of the Amazonian palm *Euterpe oleracea*. Mycologia. 86:376-385.

Rodriguez R J, White J F Jr, Arnold A E, Redman R S. 2009. Fungal endophytes: diversity and functional roles. New Phytologist. 182:314-330.

Sakalidis M L, Hardy G E S, Burgess T I. 2011. Endophytes as potential pathogens of the baobab species *Adansonia gregorii*: a focus on the Botryosphaeriaceae. Fungal Ecology. 4:1-14.

Sandberg D C, Battista L J, Arnold A E. 2014. Fungal Endophytes of Aquatic Macrophytes: Diverse Host-Generalists Characterized by Tissue Preferences and Geographic Structure. Microbial Ecology. 67:735-747.

Sato Y, Narisawa K, Tsuruta K, Umezu M, Nishizawa T, Tanaka K, Yamaguchi K, Komatsuzaki M, Ohta H. 2010. Detection of Betaproteobacteria inside the mycelium of the fungus *Mortierella elongata*. Microbes and Environments. 25:321-324.

Sharma M, Schmid M, Rothballer M, Hause G, Zuccaro A, Imani J, Kampfer P, Domann E, Schäfer P, Hartmann A, Kogel K-H. 2008. Detection and identification of bacteria intimately associated with fungi of the order Sebacinales. Cellular Microbiology. 10:2235-2246.

Sharma M, Schmid M, Rothballer M, Hause G, Zuccaro A, Imani J, Kampfer P, Domann E, Schäfer P, Hartmann A, Kogel K-H. 2008. Detection and identification of bacteria intimately associated with fungi of the order Sebacinales. Cellular Microbiology. 10:2235-2246.

Singh L P, Gill S S, Tuteja N. 2014. Unraveling the role of fungal symbionts in plant abiotic stress tolerance. Plant Signaling and Behavior. 6:175-191.

Smith F A, Grace E J, Smith S E. 2009. More than a carbon economy: nutrient trade and ecological sustainability in facultative arbuscular mycorrhizal symbioses. New Phytologist. 182:347-358.

Stone J K, Bacon C W, White J F. 2000. An overview of endophytic microbes: endophytism defined. Microbial Endophytes. In: Microbial endophytes. Marcel Dekker, New York.

Strobel G, Daisy B, Castillo U. Harper J. 2004. Natural products from endophytic microorganisms. Journal of Natural Products. 67:257-268.

Tarkka M T, Sarniguet A, Frey-Klett P. 2009. Inter-kingdom encounters: recent advances in molecular bacterium-fungus interactions. Current Genetics. 55:233-243.

Turner T R, James E K, Poole P S. 2013. The plant microbiome. Genome Biology. 14:209.

U'Ren J M, Lutzoni F, Miadlikowska J, Laetsch A D, Arnold A E. 2012. Host and geographic structure of endophytic and endolichenic fungi at a continental scale. American Journal of Botany. 99:898-914.

van der Putten W H, Klironomos J N, Wardle D A. 2007. Microbial ecology of biological invasions. ISME Journal 1:28-37.

Waller F, Achatz B, Baltruschat H, Fodor J, Becker K, Fischer M, Heier T, Hickelhoven R, Neumann C, Wettstein von D, Franken P, Kogel K-H. 2005. The endophytic fungus *Piriformospora indica* reprograms barley to salt-stress tolerance, disease resistance, and higher yield. Proceedings of the National Academy of Sciences of the United States of America. 102:13386-13391.

Wikee S, Jaidee P, Wongkam S, Mckenzie E, Hyde K, Chukeatirote E. 2013. Antimicrobial activity of crude extracts of *Phyllosticta* spp. Mycology. 4:112-117.

Xiao J, Zhang Q, Gao Y Q, Tang J J, Zhang A L, Gao J M. 2014. Secondary metabolites from the endophytic *Botryosphaeria dothidea* of *Melia azedarach* and their antifungal, antibacterial, antioxidant, and cytotoxic activities. Journal of Agricultural and Food Chemistry. 62:3584-3590.

Zimmerman N B, Vitousek P M. 2012. Fungal endophyte communities reflect environmental structuring across a Hawaiian landscape. Proceedings of the National Academy of Sciences of the United States of America. 109: 13022-13027.

What is claimed is:

1. A method for examining phenotypic changes in a cultured endophytic fungi of the phylum Ascomyota comprising
producing a cured endophytic fungus by treating a first endophytic fungus from culture of the phylum Ascomyota to cure the fungus of its native endohyphal bacteria by applying to the fungus antibiotic to produce a cured endophytic fungus, and
measuring and comparing phenotypic activity of the first endophytic fungus before treatment with the antibiotic to phenotypic activity of the cured endophytic fungus, to determine the bacteria's effect on the fungus' phenotype wherein the phenotypic activity is selected from the group consisting of cellulase activity, ligninase activity and a combination of cellulase and ligninase activity.

2. The method of claim 1, further comprising
inoculating the cured endophytic fungus with non-native endohyphal bacteria to resynthesize the cured endophytic fungus with endohyphal bacteria to produce a resynthesized fungus, and
comparing the phenotypic activity of the cured endophytic fungus to phenotypic activity of the resynthesized fungus.

3. The method of claim 2, wherein the first endophytic fungus is selected from the group consisting of *Microdiplodia, Alternaria, Cladosporium* and *Pestalotiopsis*.

4. The method of claim 2, wherein the non-native endohyphal bacteria is selected from the group consisting of *Erwinia, Luteibacter*, and *Sphingomonas*.

5. The method of claim 1, further comprising
inoculating the cured endophytic fungus with non-native endohyphal bacteria to resynthesize the cured endophytic fungus with endohyphal bacteria to produce a resynthesized fungus, and
comparing the phenotypic activity of the first endophytic fungus to phenotypic activity of the resynthesized fungus.

6. The method of claim 5, wherein the first endophytic fungus is selected from the group consisting of *Microdiplodia, Alternaria, Cladosporium* and *Pestalotiopsis*.

7. The method of claim 5, wherein the non-native endohyphal bacteria is selected from the group consisting of *Erwinia, Luteibacter*, and *Sphingomonas*.

8. The method of claim 1, wherein the first endophytic fungus is selected from the group consisting of *Microdiplodia, Alternaria, Cladosporium* and *Pestalotiopsis*.

9. The method of claim 1, wherein the first endophytic fungus is isolated from a host plant.

10. The method of claim 1, wherein the first endophytic fungus and the cured endophytic fungus remain viable.

11. The method of claim 1, wherein the antibiotic is comprised of Ampicillin, Kanamycin, Tetracycline and Ciprofloxacin.

12. The method of claim 11, wherein the antibiotic is comprised of about 100 µg/ml Ampicillin, about 50 µg/ml Kanamycin, about 10 µg/ml Tetracycline and about 40 µg/ml Ciprofloxacin.

* * * * *